(12) United States Patent
Reiffenrath et al.

(10) Patent No.: US 6,632,484 B2
(45) Date of Patent: Oct. 14, 2003

(54) DIALKYNE COMPOUNDS

(75) Inventors: Volker Reiffenrath, Robdorf (DE); Georg Lüssem, Ober-Ramstadt (DE)

(73) Assignee: Merck Patent Gesellschaft mit beschränkter Haftung, Darmstadt (DE)

( * ) Notice: Subject to any disclaimer, the term of this patent is extended or adjusted under 35 U.S.C. 154(b) by 135 days.

(21) Appl. No.: 09/907,630

(22) Filed: Jul. 19, 2001

(65) Prior Publication Data

US 2002/0117650 A1 Aug. 29, 2002

(30) Foreign Application Priority Data

Jul. 20, 2000 (DE) .......................... 100 35 651

(51) Int. Cl.$^7$ .................. C09K 19/34; C09K 19/32; C07D 319/06; C07C 23/18; C07C 13/18; C07C 13/19

(52) U.S. Cl. .............. 428/1.1; 252/299.61; 252/299.63; 549/369; 549/373; 549/374; 570/131; 570/188; 585/534

(58) Field of Search ............ 252/299.63, 299.61; 549/369, 373, 374; 428/1.1; 570/188, 131; 585/534

(56) References Cited

U.S. PATENT DOCUMENTS 6,171,665 B1 * 1/2001 Heckmeier et al. .......... 428/1.1
6,203,724 B1 * 3/2001 Reiffenrath et al. .... 252/299.61
6,303,194 B1 * 10/2001 Reiffenrath et al. .......... 428/1.1

* cited by examiner

*Primary Examiner*—Shean C. Wu
(74) *Attorney, Agent, or Firm*—Millen, White, Zelano & Branigan, P.C.

(57) ABSTRACT

Described are dialkyne compounds of the formula I

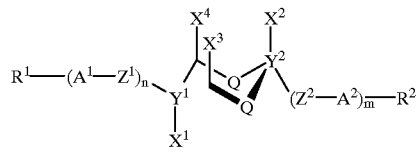

in which n, m, $R^1$, $R^2$, $X^1$, $X^2$, $X^3$, $X^4$, $Z^1$, $Z^2$, $A^1$, $A^2$, Q, $Y^1$ and $Y^2$ are as defined herein and the use of such compounds in liquid-crystal media.

19 Claims, No Drawings

DIALKYNE COMPOUNDS

The invention relates to dialkyne compounds of the formula I

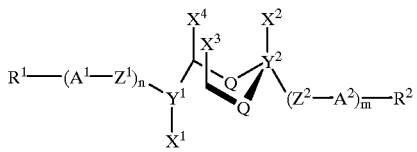

in which

R$^1$ and R$^2$, independently of one another, are H, F, or an alkyl radical having 1–15 carbon atoms which is unsubstituted or at least monosubstituted by halogen or CN and in which, in addition, one or more CH$_2$ groups may each, independently of one another, be replaced by —O—, —S—, —CO—,

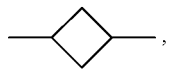

—CO—O—, —O—CO—, —O—CO—O— or —CH=CH— in such a way that heteroatoms are not connected directly, X$^1$, X$^2$, X$^3$ and X$^4$ are each, independently of one another, H or —C≡C—C≡C—R$^3$, where at least one of the groups X$^1$, X$^2$, X$^3$ and X$^4$ is —C≡C—C≡C—R$^3$, R$^3$ is H, Cl, CN, SF$_5$, CF$_3$, or an alkyl radical having 1–15 carbon atoms which is unsubstituted or at least monosubstituted by halogen and in which, in addition, one or more CH$_2$ groups may be replaced, in each case independently of one another, by —CH=CH— or —O— in such a way that —O— atoms are not connected directly, Q is —CH$_2$— or —O—, and Y$^1$ and Y$^2$, independently of one another, are C or Si, A$^1$ and A$^2$, independently of one another, are a trans-1,4-cyclohexylene radical which is unsubstituted or substituted by F or CN and in which, in addition, one or more non-adjacent CH$_2$ groups may be replaced by —O— and/or —S—, or are

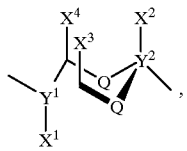

Z$^1$ and Z$^2$ are each, independently of one another, —CO—O—, —O—CO—, —CH$_2$O—, —O—, —OCH$_2$—, —CF$_2$O—, —OCF$_2$—, —CF$_2$CF$_2$—, —CF=CF—, —CH$_2$CH$_2$—, —CH=CH— or a single bond, and n and m, independently of one another, are 0, 1, 2 or 3, where m+n is 1, 2 or 3.

The invention also relates to the use of the compounds of the formula I as components of liquid-crystalline media, and to liquid-crystal and electro-optical display elements which contain the liquid-crystalline media according to the invention.

The compounds of the formula I frequently have a low positive or negative value of the dielectric anisotropy and can be used as components of liquid-crystalline media, in particular for displays based on the principle of the twisted cell, the guest-host effect, the effect of deformation of aligned phases DAP or ECB (electrically controlled birefringence) or the effect of dynamic scattering.

The substances employed hitherto for this purpose all have certain disadvantages, for example inadequate stability to the action of heat, light or electric fields, or unfavorable elastic and/or dielectric properties.

The invention has an object of finding novel stable liquid-crystalline or mesogenic compounds having particularly low optical anisotropy (Δn) and negative or positive dielectric anisotropy (Δε) which are suitable as components of liquid-crystalline media, in particular for TFT and STN displays.

Upon further study of the specification and appended claims, further objects and advantages of this invention will become apparent to those skilled in the art.

It has now been found that the compounds of the formula I are eminently suitable as components of liquid-crystalline media. With their aid, it is possible to obtain stable liquid-crystalline media, in particular suitable for TFT or STN displays. The novel compounds are distinguished, in particular, by high thermal stability, which is advantageous for a high holding ratio, and exhibit favorable clearing point values. At a reduced temperature of 0.9 and a wavelength of 589 nm, the compounds of the formula I have an optical anisotropy value Δn of <0.03, preferably <0.02, which is attributable to a particularly large value of n$_1$. The reduced temperature here is defined as follows:

$$\frac{\text{measurement temperature in } K}{\text{clearing point temperature in } K} = \text{reduced temperature}$$

Liquid-crystalline media having very low optical anisotropy values are of particular importance for reflective and transflective applications, i.e. applications in which the respective LCD experiences no or only supporting background illumination. Low values of Δn are achieved by the use of substituents X$^1$, X$^2$, X$^3$ and/or X$^4$ having the highest possible polarizability. Owing to the small volume of the groups X$^1$, X$^2$, X$^3$ and X$^4$, the other LC properties, such as clearing point and viscosity, of liquid-crystalline mixtures to which the compounds according to the invention have been added are only impaired to a relatively small extent.

Very generally, the provision of compounds of the formula I considerably broadens the range of liquid-crystalline substances which are suitable, from various applicational points of view, for the preparation of liquid-crystalline mixtures.

The compounds of the formula I have a broad range of applications. Depending on the choice of substituents, these compounds can serve as base materials of which liquid-crystalline media are predominantly composed; however, it is also possible to add compounds of the formula I to liquid-crystalline base materials from other classes of compound in order, for example, to modify the dielectric and/or optical anisotropy of a dielectric of this type and/or to optimise its threshold voltage and/or its viscosity. Addition of compounds of the formula I to liquid-crystalline dielectrics enables Δn values of such media to be significantly reduced.

The meaning of the formula I includes all isotopes of the chemical elements bound in the compounds of the formula I. In enantiomerically pure or enriched form, the compounds of the formula I are also suitable as chiral dopants and in general for achieving chiral mesophases.

In the pure state, the compounds of the formula I are colorless and form liquid-crystalline mesophases in a temperature range which is favorably located for electro-optical use. They are stable chemically, thermally and to light.

The invention thus relates to the compounds of the formula I and to the use of these compounds as components of liquid-crystalline media. The invention furthermore relates to liquid-crystalline media comprising at least one compound of the formula I and to liquid-crystal display elements, in particular electro-optical display elements, which contain media of this type.

Above and below, n, m, $R^1$, $R^2$, $R^3$, $X^1$, $X^2$, $X^3$, $X^4$, $Z^1$, $Z^2$, $A^1$, $A^2$, Q, $Y^1$ and $Y^2$ are as defined above, unless expressly stated otherwise. If the radical $X^1$ occurs more than once, it may adopt identical or different meanings. The same applies to all other groups which occur more than once.

For reasons of simplicity, Cyc below denotes a cyclohexane-1,4-diyl radical or a 1- or 4-silacyclohexane-1,4-diyl radical, Dio denotes a 1,3-dioxane-2,5-diyl radical, Dit denotes a 1,3-dithiane-2,5-diyl radical, and Boc denotes a bicyclo[2,2,2]octylene radical, where Cyc may be unsubstituted or monosubstituted or polysubstituted by F or CN.

W denotes the following structural unit:

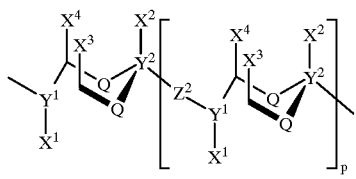

in which $X^1$, $X^2$, $X^3$, $X^4$, Q, $Y^1$, $Y^2$ and $Z^2$ are as defined above, and p is 0, 1, 2 or 3.

Preferred meanings of the group W are represented by the sub-formulae W1 to W7:

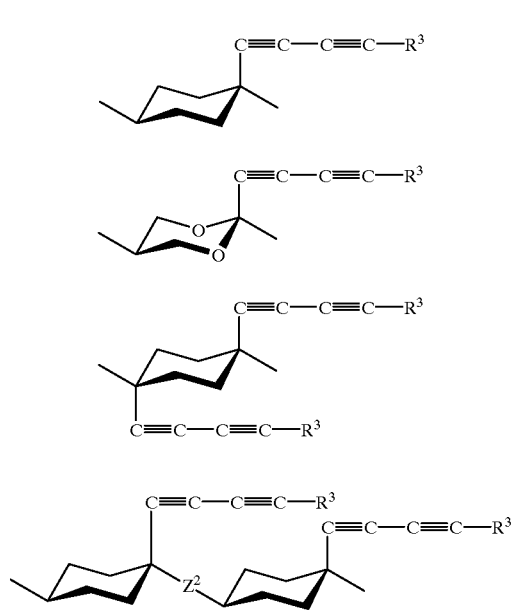

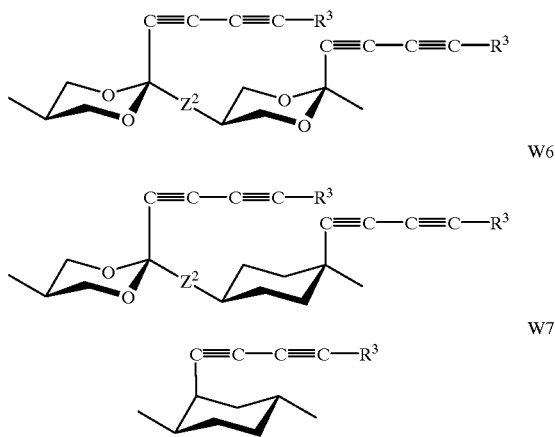

in which $Z^2$ and $R^3$ are as defined above.

Formula I covers the preferred compounds of the sub-formulae Ia1 to Ia12, which, besides the group W, contain a six-membered ring:

| | |
|---|---|
| $R^1$-W-Cyc-$R^2$ | Ia1 |
| $R^1$-W-CH$_2$CH$_2$-Cyc-$R^2$ | Ia2 |
| $R^1$-W-COO-Cyc-$R^2$ | Ia3 |
| $R^1$-W-Dio-$R^2$ | Ia4 |
| $R^1$-W-CH$_2$CH$_2$-Dio-$R^2$ | Ia5 |
| $R^1$-W-COO-Dio-$R^2$ | Ia6 |
| $R^1$-Cyc-W-$R^2$ | Ia7 |
| $R^1$-Dio-W-$R^2$ | Ia8 |
| $R^1$-Cyc-CH$_2$CH$_2$-W-$R^2$ | Ia9 |
| $R^1$-Dio-CH$_2$CH$_2$-W-$R^2$ | Ia10 |
| $R^1$-Cyc-COO-W-$R^2$ | Ia11 |
| $R^1$-Dio-COO-W-$R^2$ | Ia12 | furthermore the likewise preferred compounds of the sub-formulae Ib1 to Ib72, which, in addition to the group W, contain two six-membered rings:

| | |
|---|---|
| $R^1$-Cyc-Cyc-W-$R^2$ | Ib1 |
| $R^1$-Dio-Cyc-W-$R^2$ | Ib2 |
| $R^1$-Cyc-CH$_2$CH$_2$-Cyc-W-$R^2$ | Ib3 |
| $R^1$-Dio-CH$_2$CH$_2$-Cyc-W-$R^2$ | Ib4 |
| $R^1$-Cyc-COO-Cyc-W-$R^2$ | Ib5 |
| $R^1$-Dio-COO-Cyc-W-$R^2$ | Ib6 |
| $R^1$-Cyc-Dio-W-$R^2$ | Ib7 |
| $R^1$-Dio-Dio-W-$R^2$ | Ib8 |
| $R^1$-Cyc-CH$_2$CH$_2$-W-$R^2$ | Ib9 |
| $R^1$-Dio-CH$_2$CH$_2$-W-$R^2$ | Ib10 |
| $R^1$-Cyc-COO-Dio-W-$R^2$ | Ib11 |
| $R^1$-Dio-COO-Dio-W-$R^2$ | Ib12 |
| $R^1$-Cyc-Cyc-CH$_2$CH$_2$-W-$R^2$ | Ib13 |
| $R^1$-Dio-Cyc-CH$_2$CH$_2$-W-$R^2$ | Ib14 |
| $R^1$-Cyc-Dio-CH$_2$CH$_2$-W-$R^2$ | Ib15 |
| $R^1$-Dio-Dio-CH$_2$CH$_2$-W-$R^2$ | Ib16 |
| $R^1$-Cyc-Cyc-COO-W-$R^2$ | Ib17 |
| $R^1$-Dio-Cyc-COO-W-$R^2$ | Ib18 |
| $R^1$-Cyc-Dio-COO-W-$R^2$ | Ib19 |
| $R^1$-Dio-Dio-COO-W-$R^2$ | Ib20 |
| $R^1$-Cyc-W-Cyc-$R^2$ | Ib21 |
| $R^1$-Dio-W-Cyc-$R^2$ | Ib22 |
| $R^1$-Cyc-CH$_2$CH$_2$-W-Cyc-$R^2$ | Ib23 |
| $R^1$-Dio-CH$_2$CH$_2$-W-Cyc-$R^2$ | Ib24 |
| $R^1$-Cyc-COO-W-Cyc-$R^2$ | Ib25 |
| $R^1$-Dio-COO-W-Cyc-$R^2$ | Ib26 |
| $R^1$-Cyc-W-CH$_2$CH$_2$-Cyc-$R^2$ | Ib27 |

-continued

| | |
|---|---|
| $R^1$-Dio-W-CH$_2$CH$_2$-Cyc-$R^2$ | Ib28 |
| $R^1$-Cyc-W-COO-Cyc-$R^2$ | Ib29 |
| $R^1$-Dio-W-COO-Cyc-$R^2$ | Ib30 |
| $R^1$-Cyc-W-Dio-$R^2$ | Ib31 |
| $R^1$-Dio-W-Dio-$R^2$ | Ib32 |
| $R^1$-Cyc-CH$_2$CH$_2$-W-Dio-$R^2$ | Ib33 |
| $R^1$-Dio-CH$_2$CH$_2$-W-Dio-$R^2$ | Ib34 |
| $R^1$-Cyc-COO-W-Dio-$R^2$ | Ib35 |
| $R^1$-Dio-COO-W-Dio-$R^2$ | Ib36 |
| $R^1$-Cyc-W-CH$_2$CH$_2$-Dio-$R^2$ | Ib37 |
| $R^1$-Dio-W-CH$_2$CH$_2$-Dio-$R^2$ | Ib38 |
| $R^1$-Cyc-W-COO-Dio-$R^2$ | Ib39 |
| $R^1$-Dio-W-COO-Dio-$R^2$ | Ib40 |
| $R^1$-W-Cyc-Cyc-$R^2$ | Ib41 |
| $R^1$-W-CH$_2$CH$_2$-Cyc-Cyc-$R^2$ | Ib42 |
| $R^1$-W-COO-Cyc-Cyc-$R^2$ | Ib43 |
| $R^1$-W-Dio-Cyc-$R^2$ | Ib44 |
| $R^1$-W-CH$_2$CH$_2$-Dio-Cyc-$R^2$ | Ib45 |
| $R^1$-W-COO-Dio-Cyc-$R^2$ | Ib46 |
| $R^1$-W-Cyc-CH$_2$CH$_2$-Cyc-$R^2$ | Ib47 |
| $R^1$-W-Dio-CH$_2$CH$_2$-Cyc-$R^2$ | Ib48 |
| $R^1$-W-Cyc-COO-Cyc-$R^2$ | Ib49 |
| $R^1$-W-Dio-COO-Cyc-R | Ib50 |
| $R^1$-W-Cyc-Dio-$R^2$ | Ib51 |
| $R^1$-W-CH$_2$CH$_2$-Cyc-Dio-$R^2$ | Ib52 |
| $R^1$-W-COO-Cyc-Dio-$R^2$ | Ib53 |
| $R^1$-W-Dio-Dio-$R^2$ | Ib54 |
| $R^1$-W-CH$_2$CH$_2$-Dio-Dio-$R^2$ | Ib55 |
| $R^1$-W-COO-Dio-Dio-$R^2$ | Ib56 |
| $R^1$-W-Cyc-CH$_2$CH$_2$-Dio-$R^2$ | Ib57 |
| $R^1$-W-Dio-CH$_2$CH$_2$-Dio-$R^2$ | Ib58 |
| $R^1$-W-Cyc-COO-Dio-$R^2$ | Ib59 |
| $R^1$-W-Dio-COO-Dio-$R^2$ | Ib60 |
| $R^1$-Cyc-CH$_2$CH$_2$-W-CH$_2$CH$_2$-Cyc-$R^2$ | Ib61 |
| $R^1$-Dio-CH$_2$CH$_2$-W-CH$_2$CH$_2$-Cyc-$R^2$ | Ib62 |
| $R^1$-Cyc-CH$_2$CH$_2$-W-CH$_2$CH$_2$-Dio-$R^2$ | Ib63 |
| $R^1$-Dio-CH$_2$CH$_2$-W-CH$_2$CH$_2$-Dio-$R^2$ | Ib64 |
| $R^1$-Cyc-CH$_2$CH$_2$-Cyc-CH$_2$CH$_2$-W-$R^2$ | Ib65 |
| $R^1$-Dio-CH$_2$CH$_2$-Cyc-CH$_2$CH$_2$-W-$R^2$ | Ib66 |
| $R^1$-Cyc-CH$_2$CH$_2$-Dio-CH$_2$CH$_2$-W-$R^2$ | Ib67 |
| $R^1$-Dio-CH$_2$CH$_2$-Dio-CH$_2$CH$_2$-W-$R^2$ | Ib68 |
| $R^1$-W-CH$_2$CH$_2$-Cyc-CH$_2$CH$_2$-Cyc-$R^2$ | Ib69 |
| $R^1$-W-CH$_2$CH$_2$-Dio-CH$_2$CH$_2$-Cyc-$R^2$ | Ib70 |
| $R^1$-W-CH$_2$CH$_2$-Cyc-CH$_2$CH$_2$-Dio-$R^2$ | Ib71 |
| $R^1$-W-CH$_2$CH$_2$-Dio-CH$_2$CH$_2$-Dio-$R^2$ | Ib72 | and the preferred compounds of the sub-formulae 1c1 to 1c55, which, besides the group W, contain three six-membered rings:

| | |
|---|---|
| $R^1$-W-Cyc-Cyc-Cyc-$R^2$ | Ic1 |
| $R^1$-W-CH$_2$CH$_2$-Cyc-Cyc-Cyc-$R^2$ | Ic2 |
| $R^1$-W-Dio-Cyc-Cyc-$R^2$ | Ic3 |
| $R^1$-W-CH$_2$CH$_2$-Dio-Cyc-Cyc-$R^2$ | Ic4 |
| $R^1$-W-Cyc-CH$_2$CH$_2$-Cyc-Cyc-$R^2$ | Ic5 |
| $R^1$-W-Dio-CH$_2$CH$_2$-Cyc-Cyc-$R^2$ | Ic6 |
| $R^1$-W-Cyc-Cyc-CH$_2$CH$_2$-Cyc-$R^2$ | Ic7 |
| $R^1$-W-Dio-Cyc-CH$_2$CH$_2$-Cyc-$R^2$ | Ic8 |
| $R^1$-W-Cyc-Dio-Cyc-$R^2$ | Ic9 |
| $R^1$-W-CH$_2$CH$_2$-Cyc-Dio-Cyc-$R^2$ | Ic10 |
| $R^1$-W-Dio-Dio-Cyc-$R^2$ | Ic11 |
| $R^1$-W-CH$_2$CH$_2$-Dio-Dio-Cyc-$R^2$ | Ic12 |
| $R^1$-W-CH$_2$CH$_2$-Dio-Dio-Cyc-$R^2$ | Ic13 |
| $R^1$-W-Dio-CH$_2$CH$_2$-Dio-Cyc-$R^2$ | Ic14 |
| $R^1$-W-Cyc-CH$_2$CH$_2$-Dio-Cyc-$R^2$ | Ic15 |
| $R^1$-Cyc-Dio-CH$_2$CH$_2$-Cyc-W-$R^2$ | Ic16 |
| $R^1$-Dio-Dio-CH$_2$CH$_2$-Cyc-W-$R^2$ | Ic17 |
| $R^1$-Cyc-Cyc-Cyc-CH$_2$CH$_2$-W-$R^2$ | Ic18 |
| $R^1$-Dio-Cyc-Cyc-CH$_2$CH$_2$-W-$R^2$ | Ic19 |
| $R^1$-Cyc-Dio-Cyc-CH$_2$CH$_2$-W-$R^2$ | Ic20 |
| $R^1$-Dio-Dio-Cyc-CH$_2$CH$_2$-W-$R^2$ | Ic21 |
| $R^1$-Cyc-Cyc-Dio-W-$R^2$ | Ic22 |
| $R^1$-Dio-Cyc-Dio-W-$R^2$ | Ic23 |
| $R^1$-Cyc-CH$_2$CH$_2$-Cyc-Dio-W-$R^2$ | Ic24 |
| $R^1$-Dio-CH$_2$CH$_2$-Cyc-Dio-W-$R^2$ | Ic25 |
| $R^1$-Cyc-Dio-Dio-W-$R^2$ | Ic26 |
| $R^1$-Dio-Dio-Dio-W-$R^2$ | Ic27 |
| $R^1$-Cyc-CH$_2$CH$_2$-Dio-Dio-W-$R^2$ | Ic28 |
| $R^1$-Dio-CH$_2$CH$_2$-Dio-Dio-W-$R^2$ | Ic29 |
| $R^1$-Cyc-Cyc-CH$_2$CH$_2$-Dio-W-$R^2$ | Ic30 |
| $R^1$-Dio-Cyc-CH$_2$CH$_2$-Dio-W-$R^2$ | Ic31 |
| $R^1$-Cyc-CH$_2$CH$_2$-Dio-W-Dio-$R^2$ | Ic32 |
| $R^1$-Dio-CH$_2$CH$_2$-Dio-W-Dio-$R^2$ | Ic33 |
| $R^1$-Cyc-Cyc-CH$_2$CH$_2$-W-Dio-$R^2$ | Ic34 |
| $R^1$-Dio-Cyc-CH$_2$CH$_2$-W-Dio-$R^2$ | Ic35 |
| $R^1$-Cyc-Dio-CH$_2$CH$_2$-W-Dio-$R^2$ | Ic36 |
| $R^1$-Dio-Dio-CH$_2$CH$_2$-W-Dio-$R^2$ | Ic37 |
| $R^1$-Cyc-Cyc-W-CH$_2$CH$_2$-Dio-$R^2$ | Ic38 |
| $R^1$-Dio-Cyc-W-CH$_2$CH$_2$-Dio-$R^2$ | Ic39 |
| $R^1$-Cyc-Dio-W-CH$_2$CH$_2$-Dio-$R^2$ | Ic40 |
| $R^1$-Dio-Dio-W-CH$_2$CH$_2$-Dio-$R^2$ | Ic41 |
| $R^1$-Cyc-W-Dio-CH$_2$CH$_2$-Cyc-$R^2$ | Ic42 |
| $R^1$-Dio-W-Dio-CH$_2$CH$_2$-Cyc-$R^2$ | Ic43 |
| $R^1$-Cyc-W-Cyc-Dio-$R^2$ | Ic44 |
| $R^1$-Dio-W-Cyc-Dio-$R^2$ | Ic45 |
| $R^1$-Cyc-CH$_2$CH$_2$-W-Cyc-Dio-$R^2$ | Ic46 |
| $R^1$-Dio-CH$_2$CH$_2$-W-Cyc-Dio-$R^2$ | Ic47 |
| $R^1$-Cyc-W-CH$_2$CH$_2$-Cyc-Dio-$R^2$ | Ic48 |
| $R^1$-Dio-W-CH$_2$CH$_2$-Cyc-Dio-$R^2$ | Ic49 |
| $R^1$-Cyc-W-Cyc-CH$_2$CH$_2$-Dio-$R^2$ | Ic50 |
| $R^1$-Dio-W-Cyc-CH$_2$CH$_2$-Dio-$R^2$ | Ic51 |
| $R^1$-Cyc-W-Dio-Dio-$R^2$ | Ic52 |
| $R^1$-Dio-W-Dio-Dio-$R^2$ | Ic53 |
| $R^1$-Cyc-CH$_2$CH$_2$-W-Dio-Dio-$R^2$ | Ic54 |
| $R^1$-Dio-CH$_2$CH$_2$-W-Dio-Dio-$R^2$ | Ic55 | in which $R^1$, $R^2$, Cyc, Dio and W are as defined above.

Preference is given to compounds of the formula I which contain no isolated or aromatic C, C double bonds.

$R^1$ and $R^2$ are preferably, independently of one another, F, OCF$_3$, CF$_3$, straight-chain alkyl or alkoxy having 1 to 15 carbon atoms, in particular alkyl, alkenyl, alkenyloxy or alkoxy having up to 7 carbon atoms. In particular, preferably only one of the radicals $R^1$ and $R^2$ is a straight-chain alkenyl, alkoxy, alkenyl or alkenyloxy radical having up to 7 carbon atoms.

In preferred compounds of the formula I, $X^1$, $X^2$, $X^3$ and/or $X^4$ are —C≡C—C≡C—H, —C≡C—C≡C—alkyl, —C≡C—C≡C—Cl or —C≡C—C≡C—CN, where alkyl is an alkyl radical having to 1 to 15 carbon atoms. In particular, the alkyl radical is branched and is preferably tert-butyl.

In particularly preferred compounds of the formula I, $X^3$ and $X^4$ are simultaneously H.

Preference is furthermore given to compounds of the formula I in which only one of the groups $X^1$, $X^2$, $X^3$ and $X^4$ is not H.

—C≡C—C≡C—$R^3$ is preferably —C≡C—C≡C—C(alkyl*)$_3$, —C≡C—C≡C—C(alkyl*)(alkyl**)$_2$ or —C≡C—C≡C—CH(alkyl*)$_2$, in particular —C≡C—C≡C—C(CH$_3$)$_3$, —C≡C—C≡C—CH(CH$_3$)$_2$ or —C≡C—C≡C—C(CH$_3$)$_2$C$_3$H$_7$. alkyl* and alkyl** are each, independently of one another, CH$_3$, C$_2$H$_5$ or C$_3$H$_7$.

$A^1$ and/or $A^2$ are preferably Cyc or Dio.

Preference is also given to compounds of the formula I and of all sub-formulae in which $A^1$ and/or $A^2$ is cyclohexane-1,4-diyl which is mono-substituted or disubstituted by F or CN.

$A^1$ and/or $A^2$ is preferably

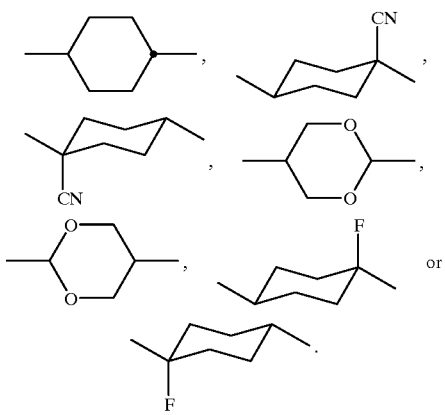

m and n are preferably 0, 1 or 2, in particular 0 or 1. m+n is preferably 1 or 2.

$Z^1$ and $Z^2$ are preferably, independently of one another, —CH$_2$CH$_2$—, —CF$_2$O—, —OCF$_2$—, —COO—, —OOC— or a single bond, particularly preferably a single bond or —CH$_2$—CH$_2$—.

Preference is given to compounds of the formula I in which $R^1$ and $R^2$ are simultaneously alkyl or alkoxy having 1 to 10 carbon atoms.

Preference is furthermore given to compounds of the formula I in which $Y^1$ and $Y^2$ are a carbon atom. Compounds of the formula I which contain not more than one dioxane ring likewise represent a preferred embodiment of the invention.

Particular preference is furthermore given to the compounds of the formulae I1 to I21 from the following group:

I1
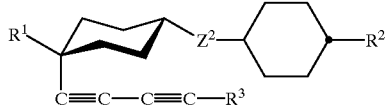

I2
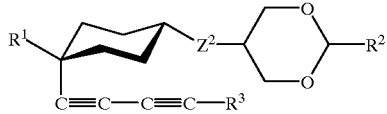

I3
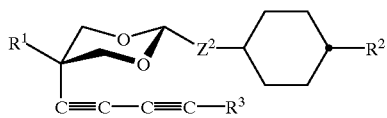

I4
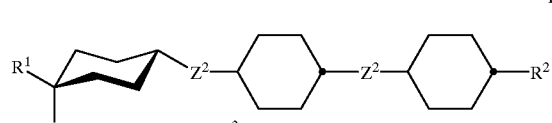

I5
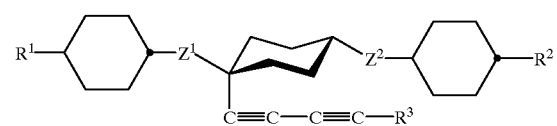

I6
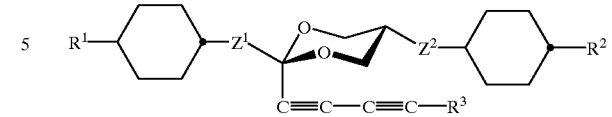

I7
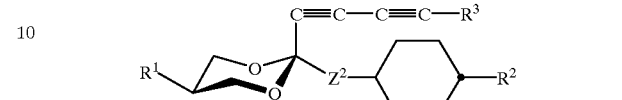

I8
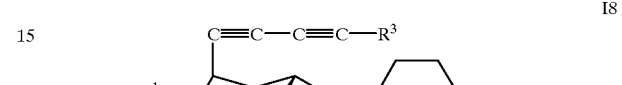

I9

I10
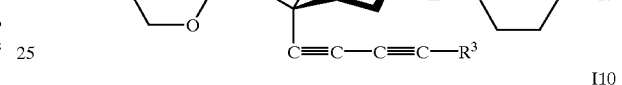

I11
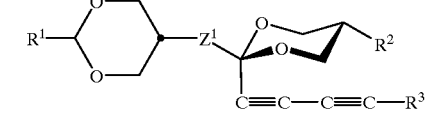

I12
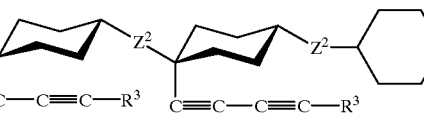

I13

I14

I15
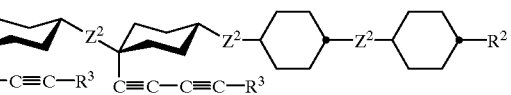

I16

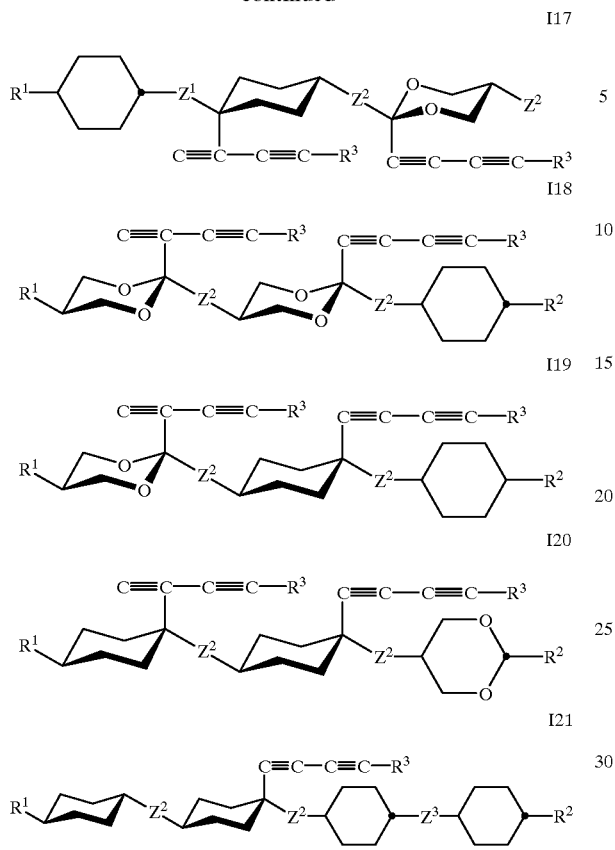

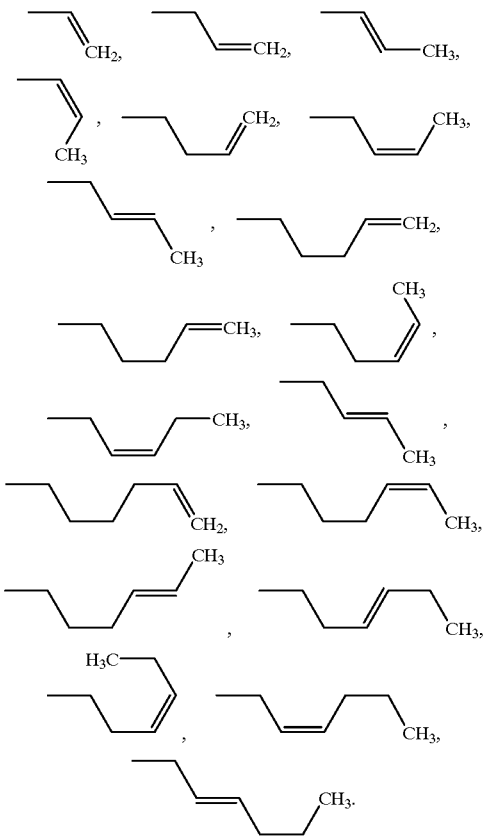

in which $R^1$, $R^2$, $R^3$, $Z^1$, and $Z^2$ are as defined above.

If $R^1$ and/or $R^2$ in the formulae above and below are an alkyl radical, this may be straight-chain or branched. It is preferably straight-chain, has 2, 3, 4, 5, 6 or 7 carbon atoms and accordingly is preferably ethyl, propyl, butyl, pentyl, hexyl or heptyl, furthermore methyl, octyl, nonyl, decyl, undecyl, dodecyl, tridecyl, tetradecyl or pentadecyl.

If $R^1$ and/or $R^2$ is an alkyl radical in which one $CH_2$ group has been replaced by —O—, this may be straight-chain or branched. It is preferably straight-chain and has 1 to 10 carbon atoms. The first $CH_2$ group in this alkyl radical has preferably been replaced by —O—, so that the radical $R^1$ attains the meaning alkoxy and is preferably methoxy, ethoxy, propoxy, butoxy, pentyloxy, hexyloxy, heptyloxy, octyloxy or nonyloxy.

It is furthermore also possible for a $CH_2$ group elsewhere to have been replaced by —O—, so that the radical $R^1$ and/or $R^2$ is preferably straight-chain 2-oxapropyl (=methoxymethyl), 2- (=ethoxymethyl) or 3-oxabutyl (=2-methoxyethyl), 2-, 3- or 4-oxapentyl, 2-, 3-, 4- or 5-oxahexyl, 2-, 3-, 4-, 5- or 6-oxaheptyl, 2-, 3-, 4-, 5-, 6- or 7-oxaoctyl, 2-, 3-, 4-, 5-, 6-, 7- or 8-oxanonyl, or 2-, 3-, 4-, 5-, 6-, 7-, 8- or 9-oxadecyl.

If $R^1$ and/or $R^2$ is an alkenyl radical, this may be straight-chain or branched. It is preferably straight-chain and has 2 to 10 carbon atoms. Accordingly, it is in particular vinyl, prop-1- or -2-enyl, but-1-, -2- or -3-enyl, pent-1-, -2-, -3- or -4-enyl, hex-1-, -2-, -3-, -4- or -5-enyl, hept-1-, -2-, -3-, -4-, -5- or -6-enyl, oct-1-, -2-, -3-, -4-, -5-, -6- or -7-enyl, non-1-, -2-, -3-, -4-, -5-, -6-, -7- or -8-enyl, or dec-1-, -2-, -3-, -4-, -5-, -6-, -7-, -8- or -9-enyl.

$R^1$ and/or $R^2$ is particularly preferably an alkenyl radical from the following group:

If $R^1$ and/or $R^2$ is an alkenyloxy radical, this may be straight-chain or branched. It is preferably straight-chain and has 2 to 10 carbon atoms. It is particularly preferably a radical from the following group:

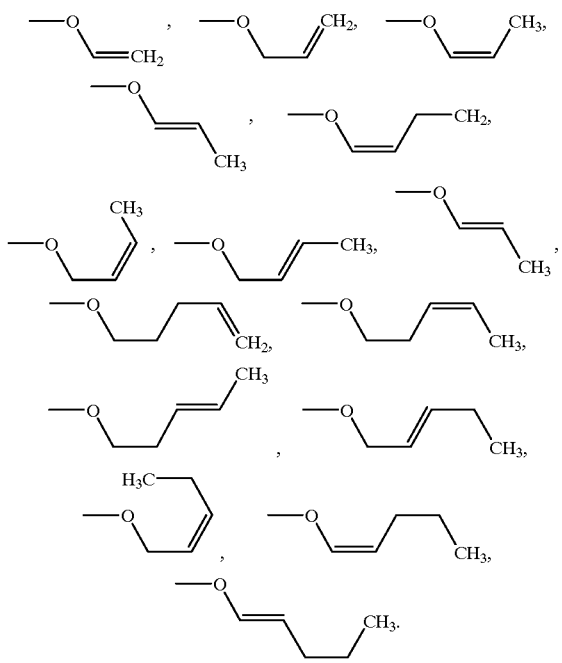

If $R^1$ and/or $R^2$ is an alkyl radical in which one $CH_2$ group has been replaced by —O— and one has been replaced by —CO—, these are preferably adjacent. These thus contain an acyloxy group —CO—O— or an oxycarbonyl group —O—CO—. These are preferably straight-chain and have 2 to 6 carbon atoms.

Accordingly, they are in particular acetoxy, propionyloxy, butyryloxy, pentanoyloxy, hexanoyloxy, acetoxymethyl, propionyloxymethyl, butyryloxymethyl, pentanoyloxymethyl, 2-acetoxyethyl, 2-propionyloxyethyl, 2-butyryloxyethyl, 3-acetoxypropyl, 3-propionyloxypropyl, 4-acetoxybutyl, methoxycarbonyl, ethoxycarbonyl, propoxycarbonyl, butoxycarbonyl, pentoxycarbonyl, methoxycarbonylmethyl, ethoxycarbonylmethyl, propoxycarbonylmethyl, butoxycarbonylmethyl, 2-(methoxycarbonyl)ethyl, 2-(ethoxycarbonyl)ethyl, 2-(propoxycarbonyl)ethyl, 3-(methoxycarbonyl)propyl, 3-(ethoxycarbonyl)propyl or 4-(methoxycarbonyl)butyl.

If $R^1$ and/or $R^2$ is an alkyl radical which is at least monosubstituted by halogen, this radical is preferably straight-chain. Halogen is preferably F or Cl. In the case of polysubstitution, halogen is preferably F. The resultant radicals also include perfluorinated radicals. In the case of monosubstitution, the fluorine or chlorine substituent may be in any desired position, but is preferably in the ω-position.

Compounds of the formula I having a branched wing group $R^1$ and/or $R^2$ may occasionally be of importance owing to better solubility in the conventional liquid-crystalline base materials, but in particular as chiral dopants if they are optically active. Smectic compounds of this type are suitable as components of ferroelectric materials.

Branched groups of this type generally contain not more than one chain branch. Preferred branched radicals $R^1$ and/or $R^2$ are isopropyl, 2-butyl (=1-methylpropyl), isobutyl (=2-methylpropyl), 2-methylbutyl, isopentyl (=3-methylbutyl), 2-methylpentyl, 3-methylpentyl, 2-ethylhexyl, 2-propylpentyl, isopropoxy, 2-methylpropoxy, 2-methylbutoxy, 3-methylbutoxy, 2-methylpentyloxy, 3-methylpentyloxy, 2-ethylhexyloxy, 1-methylhexyloxy or 1-methylheptyloxy.

Formula I covers both the racemates of these compounds and the optical antipodes, and mixtures thereof.

Of these compounds of the formula I and the sub-formulae, preference is given to those in which at least one of the radicals present therein has one of the preferred meanings indicated.

Some very particularly preferred smaller groups of compounds of the formula I are those of the sub-formulae I22 to I36:

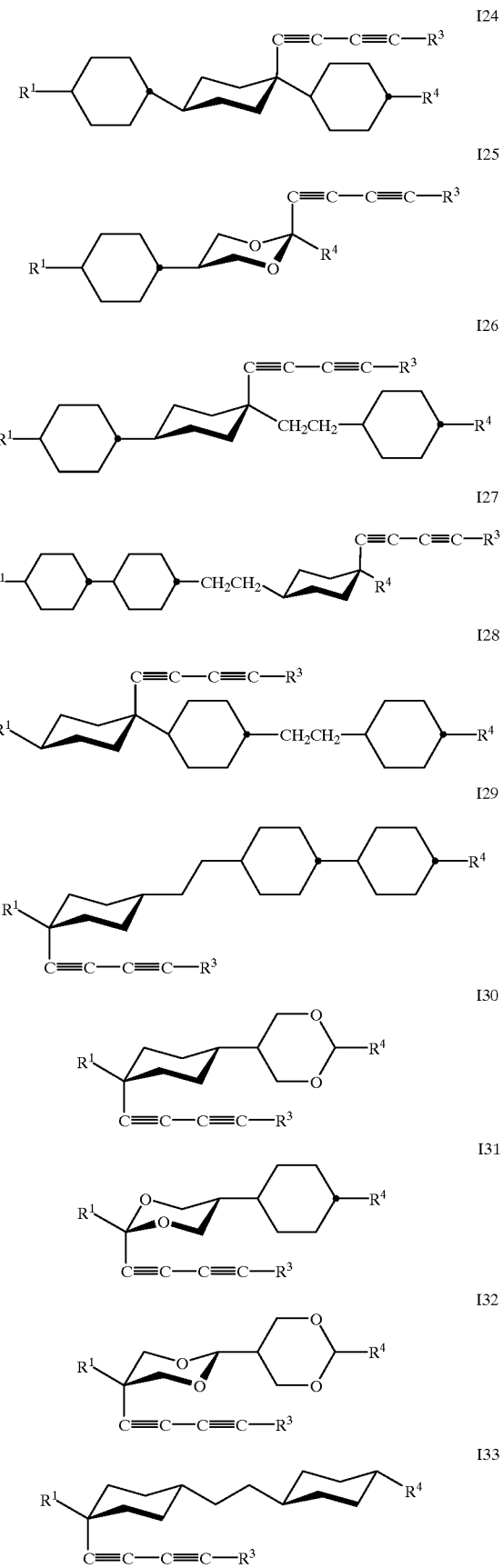

-continued

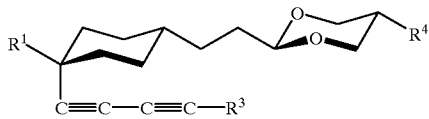
I34

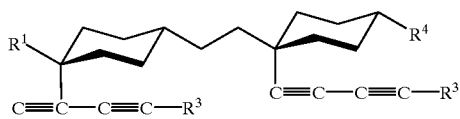
I35

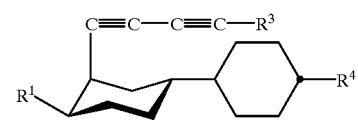
I36

The compounds of the formula I are prepared by methods known per se, as described in the literature (for example in the standard works, such as Houben-Weyl, Methoden der Organischen Chemie [Methods of Organic Chemistry], Georg-Thieme-Verlag, Stuttgart), to be precise under reaction conditions which are known and suitable for the said reactions.

Use can be made here of variants which are known per se, but are not mentioned in greater detail here.

If desired, the starting materials can also be formed in situ by not isolating them from the reaction mixture, but instead immediately converting them further into the compounds of the formula I.

The synthesis of the compounds of the formula I in which $A^1$ and/or $A^2$ is axially fluorinated cyclohexane can be effected by using hydrogen fluoride under pressure or by means of amine/hydrogen fluoride adducts (for example A. V. Grosse, C. B. Linn, J. Org. Chem. 3, (1938) 26; G. A. Olah, M. Nojima, I. Kerekes, Synthesis, (1973) 779; G. A. Olah, X-Y. Li, Q. Wang, G. K. S. Prakash, Synthesis (1993) 693).

The compounds according to the invention can be prepared, for example, in accordance with the following reaction schemes:

Scheme 1

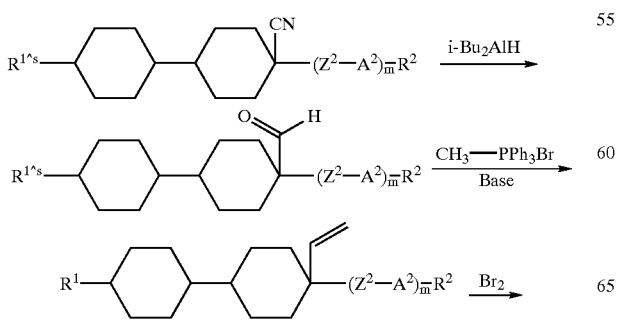

-continued

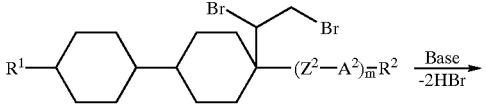

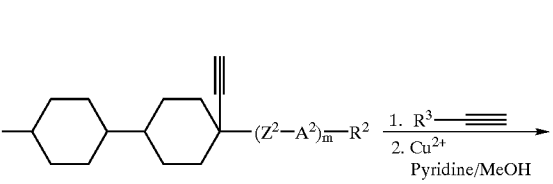

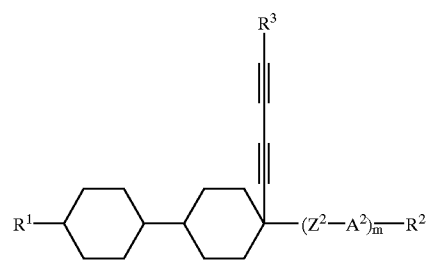

Scheme 2

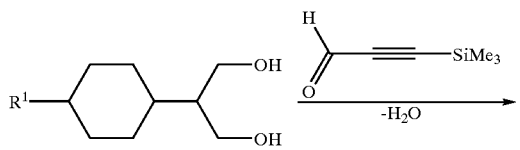

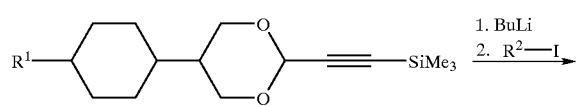

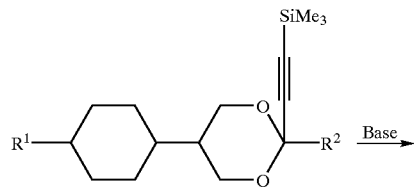

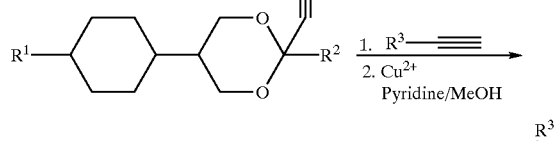

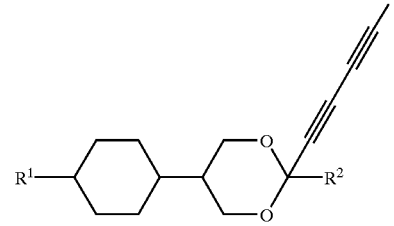

Scheme 3

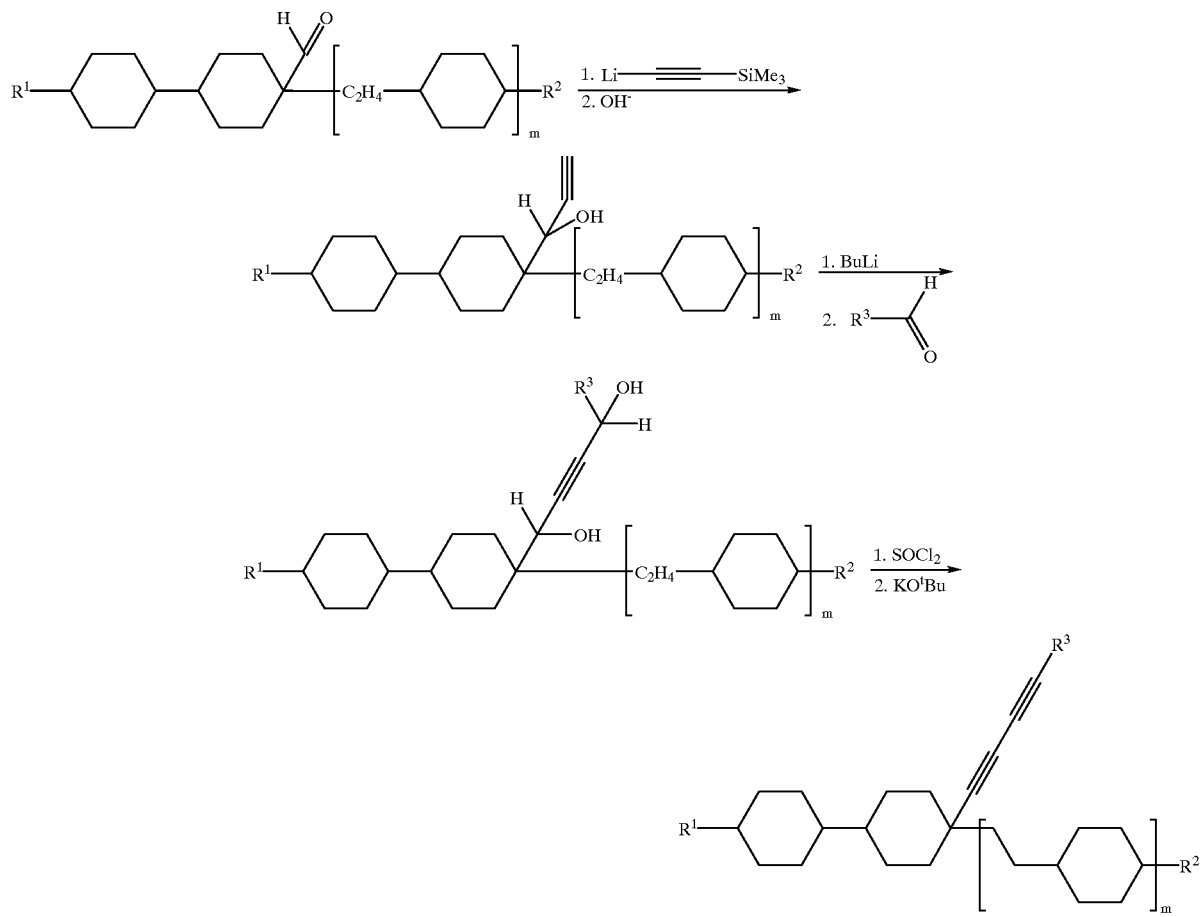

Esters of the formula I can also be obtained by esterification of corresponding carboxylic acids (or reactive derivatives thereof) using alcohols or phenols (or reactive derivatives thereof) or by the DCC method (DCC=dicyclohexylcarbodiimide).

The corresponding carboxylic acids and alcohols are known or can be prepared analogously to known processes.

Suitable reactive derivatives of the said carboxylic acids are in particular the acid halides, especially the chlorides and bromides, furthermore the anhydrides, azides or esters, in particular alkyl esters having 1–4 carbon atoms in the alkyl group.

Suitable reactive derivatives of the said alcohols are, in particular, the corresponding metal alkoxides, preferably of an alkali metal, such as Na or K.

The esterification is advantageously carried out in the presence of an inert solvent. Highly suitable solvents are, in particular, ethers, such as diethyl ether, di-n-butyl ether, THF, dioxane and anisole, ketones, such as acetone, butanone or cyclohexanone, amides, such as DMF or hexamethylphosphoric triamide, hydrocarbons, such as benzene, toluene or xylene, halogenated hydrocarbons, such as tetrachloromethane or tetrachloroethylene, and sulfoxides, such as dimethyl sulfoxide or sulfolane. Water-immiscible solvents may advantageously be used at the same time for azeotropic removal by distillation of the water formed during the esterification. An excess of an organic base, for example pyridine, quinoline or triethylamine, may occasionally also be used as solvent for the esterification. The esterification may also be carried out in the absence of a solvent, for example by simple heating of the components in the presence of sodium acetate. The reaction temperature is usually between −50° C. and +250° C., preferably between −20° C. and +80° C. At these temperatures, the esterification reactions are generally complete after from 15 minutes to 48 hours.

In detail, the reaction conditions for the esterification depend substantially on the nature of the starting materials used. Thus, a free carboxylic acid is generally reacted with a free alcohol in the presence of a strong acid, for example a mineral acid, such as hydrochloric acid or sulfuric acid. A preferred reaction procedure is the reaction of an acid anhydride or in particular an acid chloride with an alcohol, preferably in a basic medium, important bases being, in particular, alkali metal hydroxides, such as sodium hydroxide or potassium hydroxide, alkali metal carbonates or hydrogencarbonates, such as sodium carbonate, sodium hydrogencarbonate, potassium carbonate or potassium hydrogencarbonate, alkali metal acetates, such as sodium acetate or potassium acetate, alkaline earth metal hydroxides, such as calcium hydroxide, or organic bases, such as triethylamine, pyridine, lutidine, collidine or quinoline. A further preferred embodiment of the esterification comprises firstly converting the alcohol into the sodium alkoxide or potassium alkoxide, for example by treatment with ethanolic sodium hydroxide solution or potassium hydroxide solution, isolating this alkoxide, and reacting it with an acid anhydride or in particular an acid chloride.

Nitriles can be obtained by replacement of halogens using copper cyanide or alkali metal cyanide.

Ethers of the formula I are obtainable by etherification of corresponding hydroxyl compounds, the hydroxyl compound advantageously firstly being converted into a corresponding metal derivative, for example into the corresponding alkali metal alkoxide by treatment with NaH, $NaNH_2$, NaOH, KOH, $Na_2CO_3$ or $K_2CO_3$. This alkali metal alkoxide can then be reacted with the corresponding alkyl halide, alkyl sulfonate or dialkyl sulfate, advantageously in an inert solvent, such as, for example, acetone, 1,2-dimethoxyethane, DMF or dimethyl sulfoxide, or also with an excess of aqueous or aqueous-alcoholic NaOH or KOH, at temperatures between about 20° C. and 100° C.

The organometallic compounds are prepared, for example, by metal-halogen exchange (for example in accordance with Org. React. 6, 339–366 (1951)) between the corresponding halogen compound and an organolithium compound, such as, preferably, tert-butyllithium or lithium naphthalenide, or by reaction with magnesium turnings.

In addition, the compounds of the formula I can be prepared by reducing a compound which conforms to the formula I, but contains one or more reducible groups and/or C—C bonds in place of H atoms.

Suitable reducible groups are preferably carbonyl groups, in particular keto groups, furthermore, for example, free or esterified hydroxyl groups or aromatically bound halogen atoms. Preferred starting materials for the reduction are compounds conforming to the formula I, but which contain a cyclohexene ring or cyclohexanone ring instead of a cyclohexane ring and/or contain a —$CH_2CH_2$— group instead of a —CH=CH— group and/or contain a —CO— group instead of a —$CH_2$— group and/or contain a free or functionally (for example in the form of its p-toluenesulfonate) modified OH group instead of an H atom.

The reduction can be carried out, for example, by catalytic hydrogenation at temperatures between about 0° C. and about 200° C. and pressures between about 1 and 200 bar in an inert solvent, for example an alcohol, such as methanol, ethanol or isopropanol, an ether, such as tetrahydrofuran (THF) or dioxane, an ester, such as ethyl acetate, a carboxylic acid, such as acetic acid, or a hydrocarbon, such as cyclohexane. Suitable catalysts are advantageously noble metals, such as Pt or Pd, which can be employed in the form of oxides (for example $PtO_2$ or PdO), on a support (for example Pd on carbon, calcium carbonate or strontium carbonate) or in finely divided form.

Ketones can also be reduced to the corresponding compounds of the formula I containing alkyl groups and/or —$CH_2CH_2$— bridges by the methods of Clemmensen (using zinc, zinc amalgam or tin and hydrochloric acid, advantageously in aqueous-alcoholic solution or in the heterogeneous phase with water/toluene at temperatures between about 80 and 120° C.) or Wolff-Kishner (using hydrazine, advantageously in the presence of alkali, such as KOH or NaOH, in a high-boiling solvent, such as diethylene glycol or triethylene glycol, at temperatures between about 100 and 200° C.).

Furthermore, reductions with complex hydrides are possible. For example, arylsulfonyloxy groups can be removed reductively using $LiAlH_4$, in particular p-toluenesulfonyloxymethyl groups can be reduced to methyl groups, advantageously in an inert solvent, such as diethyl ether or THF, at temperatures between about 0 and 100° C.

Double bonds can be hydrogenated using $NaBH_4$ or tributyltin hydride in methanol.

The starting materials are either known or can be prepared analogously to known compounds.

The liquid-crystalline media according to the invention preferably comprise from 2 to 40, in particular from 4 to 30, components as further constituents besides one or more compounds according to the invention. These media very particularly preferably comprise from 7 to 25 components besides one or more compounds according to the invention. These further constituents are preferably selected from nematic or nematogenic (monotropic or isotropic) substances, in particular substances from the classes of the azoxybenzenes, benzylideneanilines, biphenyls, terphenyls, phenyl or cyclohexyl benzoates, phenyl or cyclohexyl esters of cyclohexanecarboxylic acid, phenyl or cyclohexyl esters of cyclohexylbenzoic acid, phenyl or cyclohexyl esters of cyclohexylcyclohexanecarboxylic acid, cyclohexylphenyl esters of benzoic acid, of cyclohexanecarboxylic acid or of cyclohexylcyclohexanecarboxylic acid, phenylcyclohexanes, cyclohexylbiphenyls, phenylcyclohexylcyclohexanes, cyclohexylcyclohexanes, cyclohexylcyclohexylcyclohexenes, 1,4-biscyclohexylbenzenes, 4,4'-biscyclohexylbiphenyls, phenyl- or cyclohexylpyrimidines, phenyl- or cyclohexylpyridines, phenyl- or cyclohexyldioxanes, phenyl- or cyclohexyl-1,3-dithianes, 1,2-diphenylethanes, 1,2-dicyclohexylethanes, 1-phenyl-2-cyclohexylethanes, 1-cyclohexyl-2-(4-phenylcyclohexyl)ethanes, 1-cyclohexyl-2-biphenylylethanes, 1-phenyl-2-cyclohexylphenylethanes, optionally halogenated stilbenes, benzyl phenyl ethers, tolans, naphthalenes, decalins and substituted cinnamic acids. The 1,4-phenylene groups in these compounds may also be fluorinated.

The most important compounds suitable as further constituents of media according to the invention can be characterised by the formulae 1, 2, 3, 4 and 5:

| | |
|---|---|
| R'-L-E-R" | 1 |
| R'-L-COO-E-R" | 2 |
| R'-L-OOC-E-R" | 3 |
| R'-L-$CH_2CH_2$-E-R" | 4 |
| R'-L-C≡C-E-R" | 5 |

In the formulae 1, 2, 3, 4 and 5, L and E, which may be identical or different, are each, independently of one another, a divalent radical from the group formed by -Phe-, -Cyc-, -Phe—Phe-, -Phe-Cyc-, -Cyc—Cyc-, -Pyr-, -Dio-, -G-Phe- and -G-Cyc- and their mirror images, where Phe is unsubstituted or fluorine-substituted 1,4-phenylene, Cyc is trans-1,4-cyclohexylene or 1,4-cyclohexylene, Pyr is pyrimidine-2,5-diyl or pyridine-2,5-diyl, Dio is 1,3-dioxane-2,5-diyl, and G is 2-(trans-1,4-cyclohexyl)ethyl, pyrimidine-2,5-diyl, pyridine-2,5-diyl or 1,3-dioxane-2,5-diyl.

One of the radicals L and E is preferably Cyc, Phe or Pyr. E is preferably Cyc, Phe or Phe-Cyc. The media according to the invention preferably comprise one or more components selected from the compounds of the formulae 1, 2, 3, 4 and 5 in which L and E are selected from the group consisting of Cyc, Phe and Pyr and simultaneously one or more components selected from the compounds of the formulae 1, 2, 3, 4 and 5 in which one of the radicals L and E is selected from the group consisting of Cyc, Phe and Pyr and the other radical is selected from the group consisting of -Phe—Phe-, -Phe-Cyc-, -Cyc—Cyc-, -G-Phe- and -G-Cyc-, and optionally one or more components selected from the compounds of the formulae 1, 2, 3, 4 and 5 in which the radicals L and E are selected from the group consisting of -Phe-Cyc-, -Cyc—Cyc-, -G-Phe- and -G-Cyc-.

In a smaller sub-group of the compounds of the formulae 1, 2, 3, 4 and 5, R' and R" are each, independently of one another, alkyl, alkenyl, alkoxy, alkoxyalkyl, alkenyloxy or alkanoyloxy having up to 8 carbon atoms. This smaller sub-group is called group A below, and the compounds are referred to by the sub-formulae 1a, 2a, 3a, 4a and 5a. In most of these compounds, R' and R" are different from one another, one of these radicals usually being alkyl, alkenyl, alkoxy, alkenyloxy or alkoxyalkyl.

In another smaller sub-group of the compounds of the formulae 1, 2, 3, 4 and 5, which is known as group B, R" is —F, —Cl, —NCS or —(O)$_i$CH$_{3-(k+l)}$F$_k$Cl$_l$, where i is 0 or 1, and k and l are 1, 2 or 3; the compounds in which R" has this meaning are referred to by the sub-formulae 1b, 2b, 3b, 4b and 5b. Particular preference is given to those compounds of the sub-formulae 1b, 2b, 3b, 4b and 5b in which R" is —F, —Cl, —NCS, —CF$_3$, —OCHF$_2$ or —OCF$_3$.

In the compounds of the sub-formulae 1b, 2b, 3b, 4b and 5b, R' is as defined for the compounds of the sub-formulae 1a–5a and is preferably alkyl, alkenyl, alkoxy, alkenyloxy or alkoxyalkyl.

In a further smaller sub-group of the compounds of the formulae 1, 2, 3, 4 and 5, R" is —CN; this sub-group is referred to below as group C, and the compounds of this sub-group are correspondingly described by sub-formulae 1c, 2c, 3c, 4c and 5c. In the compounds of the sub-formulae 1c, 2c, 3c, 4c and 5c, R' is as defined for the compounds of the sub-formulae 1a–5a and is preferably alkyl, alkoxy or alkenyl.

Besides the preferred compounds of groups A, B and C, other compounds of the formulae 1, 2, 3, 4 and 5 having other variants of the proposed substituents are also customary. All these substances are obtainable by methods which are known from the literature or analogously thereto.

Besides the compounds of the formula I according to the invention, the media according to the invention preferably comprise one or more compounds selected from group A and/or group B and/or group C. The proportions by weight of the compounds from these groups in the media according to the invention are preferably

| group A: | from 0 to 90%, preferably from 20 to 90%, in particular from 30 to 90% |
| group B: | from 0 to 80%, preferably from 10 to 80%, in particular from 10 to 65% |
| group C: | from 0 to 80%, preferably from 5 to 80%, in particular from 5 to 50%, | the sum of the proportions by weight of the group A and/or B and/or C compounds present in the respective media according to the invention preferably being 5 to 90% and in particular from 10% to 90%.

The media according to the invention preferably comprise from 1 to 40%, particularly preferably from 5 to 30%, of the compounds according to the invention. Preference is furthermore given to media comprising more than 40%, in particular from 45 to 90%, of compounds according to the invention. The media preferably comprise one or two, furthermore three to four compounds according to the invention.

The media according to the invention are prepared in a manner which is conventional per se. In general, the components are dissolved in one another, advantageously at elevated temperature. By means of suitable additives, the liquid-crystalline phases according to the invention can be modified in such a way that they can be used in all types of liquid-crystal display elements that have been disclosed hitherto. Additives of this type are known to the person skilled in the art and are described in detail in the literature (H. Kelker/R. Hatz, Handbook of Liquid Crystals, Verlag Chemie, Weinheim, 1980). For example, pleochroic dyes can be added for the preparation of colored guest-host systems or substances can be added to modify the dielectric anisotropy, the viscosity and/or alignment of the nematic phases.

The entire disclosure of all applications, patents and publications, cited above and of corresponding German application No. 10035651.6, filed Jul. 20, 2000 is hereby incorporated by reference.

EXAMPLES

The following examples are intended to illustrate the invention without representing a limitation. Above and below, percentages are percent by weight. All temperatures are given in degrees Celsius. m.p. denotes melting point, cl.p.=clearing point. Furthermore, C=crystalline state, N=nematic phase, Sn=smectic phase and I=isotropic phase. The data between these symbols represent the transition temperatures. Δn denotes optical anisotropy (589 nm, 20° C.) and Δε denotes the dielectric anisotropy (1 kHz, 20° C.).

"Conventional work-up" means that water is added if necessary, the mixture is extracted with methylene chloride, diethyl ether or toluene, the phases are separated, the organic phase is dried and evaporated, and the product is purified by distillation under reduced pressure or crystallization and/or chromatography.

The following abbreviations are used:

| THF | tetrahydrofuran |
| KOtBu | potassium tert-butoxide |
| MTB ether | methyl tert-butyl ether |
| DMSO | dimethyl sulfoxide |

Example 1

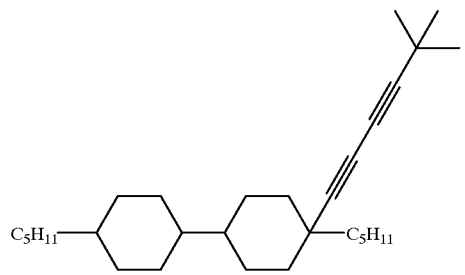

Step 1.1

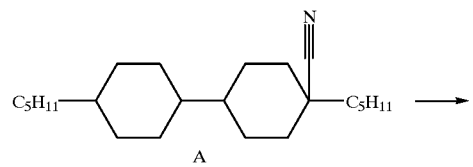

-continued

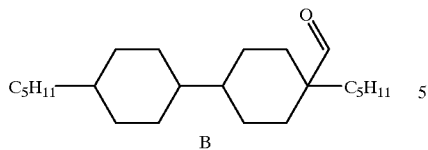
B 640 mmol of A are dissolved in 800 ml of toluene, and 755 mmol of diisobutylaluminium hydride are added dropwise to this mixture. The mixture is stirred at room temperature for about 2 hours. The reaction mixture is poured into ice/HCl, and the resultant two-phase mixture is stirred well for about 1 hour so that the resultant imine is hydrolyzed to the aldehyde. The reaction mixture is extracted with toluene, the combined organic phases are washed with water, dried over sodium sulfate and filtered, and the product is subjected to conventional work-up.

Step 1.2

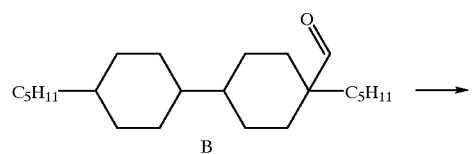
B

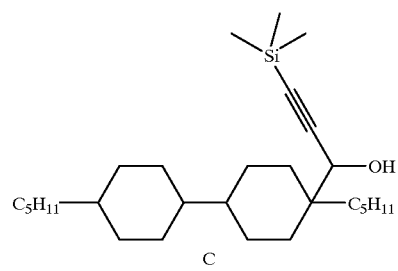
C 651 mmol of (trimethylsilyl)acetylene are dissolved in 300 ml of abs. THF, and 651 mmol of BuLi (15% solution in n-hexane) are added dropwise at from 0 to −10° C. After the mixture has been stirred for about 10 minutes, 542 mmol of B dissolved in 350 ml of abs. THF are added dropwise at from 0 to −10° C. The mixture is stirred for a further 1 hour, water is carefully added, and the mixture is subjected to conventional work-up.

Step 1.3

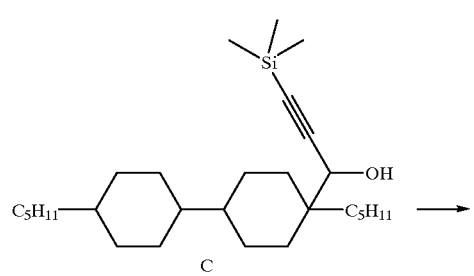
C

-continued

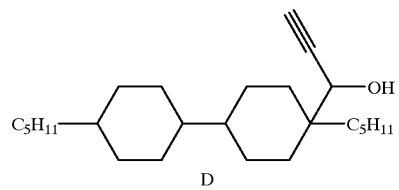
D 1.3 mol of KOH dissolved in 1500 ml of methanol are added to 0.54 mol of C. The reaction mixture is stirred at room temperature overnight, water is added, and the mixture is neutralised using HCl. Finally, the mixture is subjected to conventional work-up.

Step 1.4

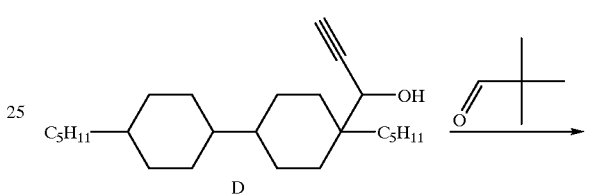
D

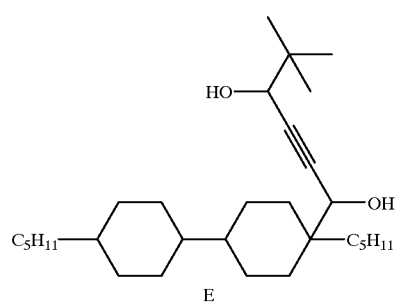
E 89 mmol of D in 100 ml of abs. THF are initially introduced, and 179 mmol of BuLi (15% solution in n-hexane) are added at from 0 to −10° C. The reaction mixture is stirred for 10 minutes, and 89 mmol of pivalaldehyde dissolved in 40 ml of abs. THF are added at from 0 to −10° C. The reaction mixture is stirred for 1 hour, water is added, and the mixture is acidified using dilute HCl and subjected to conventional work-up.

Step 1.5

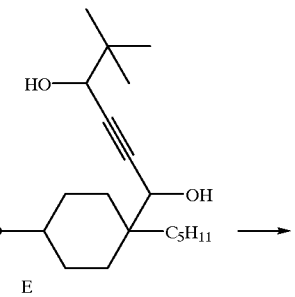
E

-continued

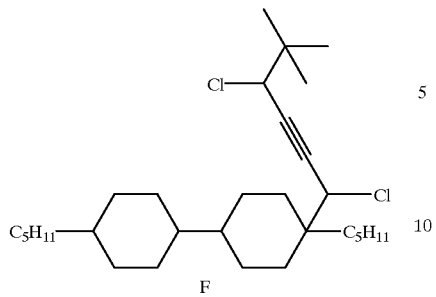

F 180 mmol of thionyl chloride are added at room temperature to 60 mmol of E dissolved in 100 ml of dichloromethanol. After the reaction mixture has been stirred for 48 hours, water is added, and the mixture is subjected to conventional work-up.

Step 1.6

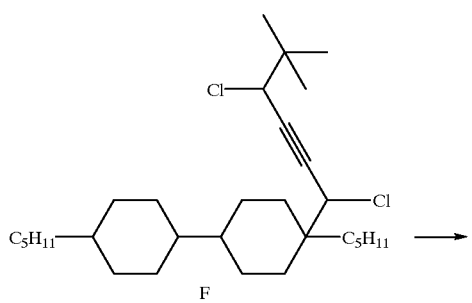

F ⟶

-continued

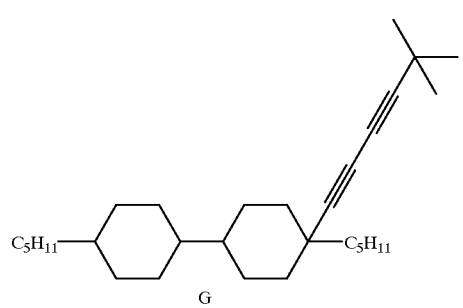

G 50 mmol of F are dissolved in 100 ml of abs. DMSO, 150 mmol of KO$^t$Bu are added in portions, and the mixture is stirred at 120° C. for 2 hours. The reaction mixture is allowed to cool, and dilute HCl is carefully added. Finally, the mixture is subjected to conventional work-up. The product is recrystallised from n-hexane/i-propanol (1:10).

C 84 N (23.6)I; Δn=−0.059; Δε=−3.8

The following compounds according to the invention are prepared analogously using the corresponding precursors:

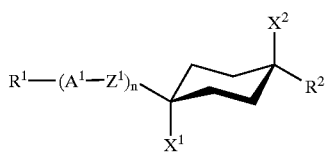

| R$^1$ | (A$^1$—Z$^1$)$_n$ | X$^2$ | X$^1$ | R$^2$ |
|---|---|---|---|---|
| n-Pentoxy | cyclohexyl | —C≡C—C≡C—CH(CH$_3$)$_2$ | H | n-Propyl |
| n-Propyl | dioxane | —C≡C—C≡C—CH$_3$ | H | OCF$_3$ |
| n-Pentyl | bicyclohexyl | —C≡C—C≡C—CH$_3$ | H | CF$_3$ |
| Ethoxy | cyclohexyl-CH$_2$CH$_2$-cyclohexyl | —C≡C—C≡C—CF$_3$ | H | F |

-continued $$R^1-(A^1-Z^1)_n-\begin{array}{c}X^2\\\diagup\\\diagdown\\X^1\end{array}R^2$$

| R¹ | (A¹—Z¹)ₙ | X² | X¹ | R² |
|---|---|---|---|---|
| n-Pentyl | (dioxane)-(cyclohexyl)- | —C≡C—C≡C—C(CH₃)₃ | H | n-Pentyloxy |
| n-Pentyl | (cyclohexyl)-(cyclohexyl)-(cyclohexyl)- | —C≡C—C≡C—CH₃ | H | CF₃CF₃ |
| H | (cyclohexyl)- | —C≡C—C≡C—C(CH₃)₃ | H | n-Propyl |
| Pentyloxy | (cyclohexyl)- | —C≡C—C≡C—CF₃ | H | CHFCF₃ |
| n-Pentyl | (cyclohexyl)- | H | —C≡C—C≡C—CF₃ | n-Propyl |
| n-Propyl | (cyclohexyl)-(cyclohexyl)-CH₂CH₂— | H | —C≡C—C≡C—C(CH₃)₃ | n-Propyl |
| n-Propyl | (dioxane)- | H | —C≡C—C≡C—CF₃ | n-Propyl |
| n-Propyl | (cyclohexyl)-(cyclohexyl)- | H | —C≡C—C≡C—C(CH₃)₃ | n-Propyl |
| Ethoxy | (cyclohexyl)-CH₂CH₂-(cyclohexyl)- | —C≡C—C≡C—CH₃ | —C≡C—C≡C—CH₃ | Methyl |
| Hexyloxy | (dioxane)-(cyclohexyl)- | H | —C≡C—C≡C—CF₃ | n-Propoxy |
| n-Pentyl | (cyclohexyl)-(cyclohexyl)-(cyclohexyl)- | —C≡CH | —C≡C—C≡C—C(CH₃)₃ | n-Propoxy |
| n-Propyl | (cyclohexyl)- | H | —C≡C—C≡C—C(CH₃)₃ | n-Propyl |
| n-Propyl | (cyclohexyl)- | H | —C≡C—C≡C—C(C₃H₇)(CH₃)₂ | n-Propyl |

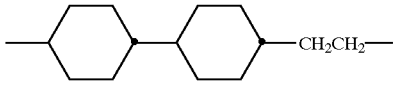

| R¹ | (A¹—Z¹)ₙ | X² | X¹ | R² |
|---|---|---|---|---|
| n-Pentyloxy | 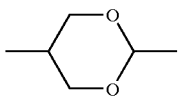 | H | —C≡C—C≡C—CF₃ | Methyl |
| n-Pentyl |  | H | —C≡C—C≡C—C(CH₃)₃ | n-Pentyl |

The following compounds according to the invention are prepared analogously using the corresponding precursors:

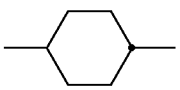

| R¹ | (Z²—A²)ₙ | X¹ | X² | R² |
|---|---|---|---|---|
| n-Propyl | 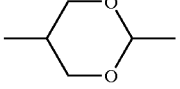 | —C≡C—C≡C—C(CH₃)₃ | H | CHFCF₃ |
| n-Pentyloxy | 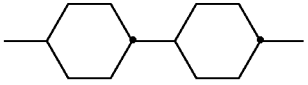 | —C≡C—C≡C—Cl | H | n-Propyl |
| n-Propyl | 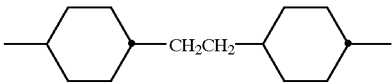 | —C≡C—C≡C—CF₃ | H | OCF₃ |
| n-Pentyl | 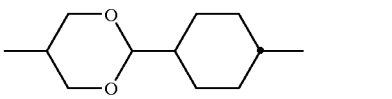 | —C≡C—C≡C—C(CH₃)₃ | H | CF₃ |
| Ethoxy | 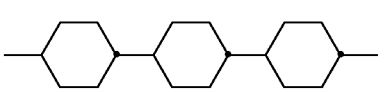 | —C≡C—C≡C—C(CH₃)₃ | H | F |
| n-Hexyloxy |  | —C≡C—C≡C—Cl | H | n-Propoxy |
| n-Pentyl | | —C≡C—C≡C—CH₃ | H | CF₂CF₃ |
| n-Propyl | | —C≡C—C≡C—C(CH₃)₃ | H | n-Propyl |

-continued

| R$^1$ | (Z$^2$—A$^2$)$_n$ | X$^1$ | X$^2$ | R$^2$ |
|---|---|---|---|---|
| n-Pentyloxy | —⟨cyclohexyl⟩— | —C≡C—C≡C—C(CH$_3$)$_3$ | H | CHFCF$_3$ |
| n-Propyl | —⟨cyclohexyl⟩— | —C≡C—C≡C—Cl | H | OCF$_3$ |

The following compounds according to the invention are prepared analogously using the corresponding precursors:

| R$^1$ | Z$^1$ | Z$^2$ | X$^1$ | X$^2$ | R$^2$ |
|---|---|---|---|---|---|
| n-Pentyloxy | — | — | —C≡C—C≡C—C(CH$_3$)$_3$ | H | CHFCF$_3$ |
| n-Propyl | — | — | —C≡C—C≡C—C(CH$_3$)$_3$ | H | n-Propyl |
| n-Propyl | —CH$_2$CH$_2$— | — | —C≡C—C≡C—CF$_3$ | H | n-Propyl |
| n-Pentyl | — | —COO— | —C≡C—C≡C—CH$_3$ | H | CF$_3$ |
| n-Propyl | —CH$_2$CH$_2$— | —CH$_2$CH$_2$— | —C≡C—C≡C—C(CH$_3$)$_3$ | —C≡C—C≡C—Cl | n-Propyl |
| n-Hexyloxy | —CH$_2$CH$_2$— | — | —C≡C—C≡C—C(CH$_3$)$_3$ | H | n-Propoxy |
| n-Pentyl | — | — | —C≡C—C≡C—Cl | H | CF$_2$CF$_3$ |
| n-Propyl | — | — | —C≡C—C≡C—C(CH$_3$)$_3$ | —C≡C—C≡C—SF$_5$ | n-Propyl |
| n-Pentyloxy | — | — | —C≡C—C≡C—C(CH$_3$)$_3$ | H | CHFCF$_3$ |
| n-Propyl | —OOC— | — | —C≡C—C≡C—CH$_3$ | H | OCF$_3$ |
| n-Propyl | —OOC— | —CH$_2$CH$_2$— | H | —C≡C—C≡C—CF$_3$ | CHFCF$_3$ |
| n-Pentyloxy | — | — | H | —C≡C—C≡C—C(CH$_3$)$_3$ | n-Pentyl |
| n-Propyl | — | —OOC— | H | —C≡C—C≡C—CH$_3$ | n-Propyl |
| n-Pentyl | —CH$_2$CH$_2$— | — | H | —C≡C—C≡C—C(CH$_3$)$_3$ | n-Propyl |
| Ethoxy | — | — | H | —C≡C—C≡C—CH$_3$ | Methyl |
| n-Hexyloxy | — | —CH$_2$CH$_2$— | H | —C≡C—C≡C—C(CH$_3$)$_3$ | n-Propoxy |
| n-Pentyl | — | — | H | —C≡C—C≡C—Cl | n-Propoxy |
| n-Propyl | CF$_2$O— | — | H | —C≡C—C≡C—H | n-Propyl |
| n-Propyl | — | —CF$_2$O— | H | —C≡C—C≡C—H | n-Propyl |
| n-Pentyl | —CF$_2$O— | — | H | —C≡C—C≡C—H | n-Pentyl |
| n-Pentyl | — | —CF$_2$O— | H | —C≡C—C≡C—H | n-Pentyl |
| n-Propyl | — | —CH$_2$CH$_2$— | H | —C≡C—C≡C—C(CH$_3$)$_3$ | n-Propyl |
| n-Pentyloxy | —OOC— | — | H | —C≡C—C≡C—C(CH$_3$)$_3$ | Methyl |
| n-Pentyl | — | — | H | —C≡C—C≡C—CH$_3$ | n-Pentyl |

The following compounds according to the invention are prepared analogously using the corresponding precursors:

| $R^1$ | $Z^1$ | $Z^2$ | $X^1$ | $X^2$ | $R^2$ |
|---|---|---|---|---|---|
| n-Pentyloxy | — | — | —C≡C—C≡C—C(CH$_3$)$_3$ | H | CHFCF$_3$ |
| n-Pentoxy | — | — | —C≡C—C≡C—Cl | | n-Propyl |
| n-Propyl | — | —CH$_2$CH$_2$— | —C≡C—C≡C—Cl | —C≡C—C≡C—Cl | OCF$_3$ |
| n-Pentyl | — | —COO— | —C≡C—C≡C—CH | H | CF$_3$ |
| Ethoxy | —CH$_2$CH$_2$— | —CH$_2$CH$_2$— | —C≡C—C≡C—C(CH$_3$)$_3$ | H | F |
| n-Hexyloxy | —CH$_2$CH$_2$— | — | —C≡C—C≡C—Cl | H | n-Propoxy |
| n-Pentyl | — | — | —C≡C—C≡C—CF$_3$ | —C≡C—C≡C—CF$_3$ | CF$_2$CF$_3$ |
| n-Propyl | — | — | —C≡C—C≡C—C(CH$_3$)$_3$ | H | n-Propyl |
| n-Pentyloxy | — | — | —C≡C—C≡C—C(CH$_3$)$_3$ | H | CHFCF$_3$ |
| n-Propyl | — | —OOC— | —C≡C—C≡C—C(CH$_3$)$_3$ | H | OCF$_3$ |
| n-Propyl | —OOC— | —CH$_2$CH$_2$— | H | —C≡C—C≡C—CH$_3$ | CHFCF$_3$ |
| n-Pentyloxy | — | — | —C≡C—C≡C—C(CH$_3$)$_3$ | —C≡C—C≡C—C(CH$_3$)$_3$ | n-Pentyl |
| n-Propyl | — | — | H | —C≡C—C≡C—C(CH$_3$)$_3$ | n-Propyl |
| n-Pentyl | —CH$_2$CH$_2$— | — | H | —C≡C—C≡C—Cl | n-Propyl |
| n-Propyl | —CF$_2$O— | — | H | —C≡C—C≡C—H | n-Propyl |
| n-Propyl | — | —CF$_2$O— | H | —C≡C—C≡C—H | n-Propyl |
| n-Propyl | —CF$_2$O— | — | H | —C≡C—C≡C—H | n-Pentyl |
| n-Propyl | — | —CF$_2$O— | H | —C≡C—C≡C—H | n-Pentyl |
| Ethoxy | — | — | —C≡C—C≡C—C(CH$_3$)$_3$ | —C≡C—C≡C—C(CH$_3$)$_3$ | Methyl |
| n-Hexyloxy | — | —CH$_2$CH$_2$— | H | —C≡C—C≡C—Cl | n-Propoxy |
| n-Pentyl | — | — | H | —C≡C—C≡C—C(CH$_3$)$_3$ | n-Propoxy |
| n-Propyl | —CH$_2$CH$_2$— | — | H | —C≡C—C≡C—C(CH$_3$)$_3$ | n-Propyl |
| n-Pentyloxy | —OOC— | — | H | —C≡C—C≡C—C(CH$_3$)$_3$ | Methyl |
| n-Pentyl | — | — | H | —C≡C—C≡C—Cl | n-Pentyl |

The following compounds according to the invention are prepared analogously using the corresponding precursors:

| $R^1$ | $(A^1—Z^1)_n$ | $X^5$ | $R^5$ |
|---|---|---|---|
| n-Propyl | —⬡—COO— | —C≡C—C≡C—C(CH$_3$)$_3$ | —OOC—⬡—n-Propyl |
| n-Pentyloxy | —⬡—COO— | —C≡C—C≡C—CH$_3$ | n-Propoxy |
| n-Propoxy | — | —C≡C—C≡C—CF$_3$ | OCF$_3$ |
| n-Pentyl | —⬡—⬡—COO— | —C≡C—C≡C—C(CH$_3$)$_3$ | OCH$_3$ |
| Ethyl | —⬡—CH$_2$O— | —C≡C—C≡C—C(CH$_3$)$_3$ | n-Propoxy |

-continued

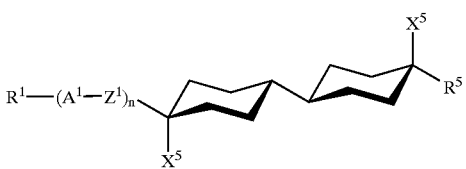

| R¹ | (A¹—Z¹)ₙ | X⁵ | R⁵ |
|---|---|---|---|
| n-Hexyl | 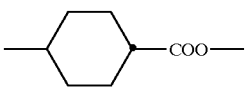—COO— | —C≡C—C≡C—C(CH₃)₃ | —OOC—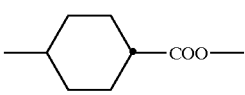—Methyl |
| n-Pentyloxy | — | —C≡C—C≡C—Cl | OCF₂CF₃ |
| n-Propyl | 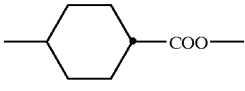—COO— | —C≡C—C≡C—C(CH₃)₃ | n-Pentyloxy |
| n-Butyl | 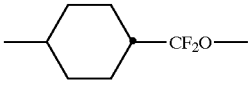—COO— | —C≡C—C≡C—C(CH₃)₃ | OCF=CF₂ |
| n-Propoxy | — | —C≡C—C≡C—C(CH₃)₃ | OCF₃ |
| n-Propyl | 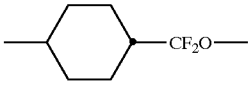—CF₂O— | —C≡C—C≡C—C(CH₃)₃ | n-Propyl |
| n-Propyl | 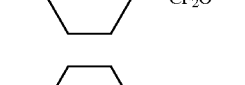—CF₂O— | —C≡C—C≡C—C(CH₃)₃ | F |
| n-Propyl | 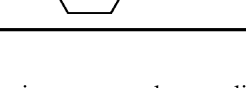—CF₂O— | —C≡C—C≡C—C(CH₃)₃ | OCF₃ |
| n-Propyl | 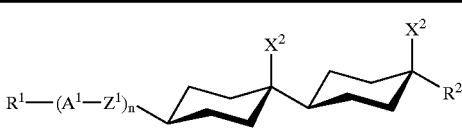—CF₂O— | —C≡C—C≡C—C(C₂H₅)₂C₃H₇ | CF₃ |

The following compounds according to the invention are prepared analogously using the corresponding precursors:

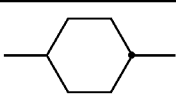

| R¹ | (A¹—Z¹)ₙ | X² | R² |
|---|---|---|---|
| n-Propyl | 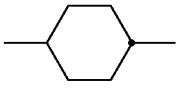 | —C≡C—C≡C—C(CH₃)₃ | CHFCF₃ |
| n-Pentyloxy | 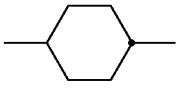 | —C≡C—C≡C—C(CH₃)₃ | n-Propyl |

-continued

R$^1$—(A$^1$—Z$^1$)$_n$—[cyclohexyl with X$^2$]—[cyclohexyl with X$^2$ and R$^2$]

| R$^1$ | (A$^1$—Z$^1$)$_n$ | X$^2$ | R$^2$ |
|---|---|---|---|
| n-Propyl | [1,3-dioxane] | —C≡C—C≡C—CH$_3$ | OCF$_3$ |
| Ethoxy | [cyclohexyl]—CH$_2$CH$_2$—[cyclohexyl] | —C≡C—C≡C—C(CH$_3$)$_3$ | F |
| n-Hexyloxy | [1,3-dioxane]—[cyclohexyl] | —C≡C—C≡C—C(CH$_3$)$_3$ | n-Propoxy |
| n-Propyl | [cyclohexyl] | —C≡C—C≡C—CF$_3$ | n-Propyl |
| n-Pentyloxy | [cyclohexyl] | —C≡C—C≡C—C(CH$_3$)$_3$ | CHFCF$_3$ |
| n-Propyl | [1,3-dioxane] | —C≡C—C≡C—CH$_3$ | OCF$_3$ |
| n-Propyl | [cyclohexyl]—CF$_2$O— | —C≡C—C≡C—CH$_3$ | CF$_3$ |
| n-Propyl | [cyclohexyl]—CF$_2$O— | —C≡C—C≡C—CH$_3$ | F |

The following compounds according to the invention are prepared analogously using the corresponding precursors:

R$^1$—(A$^1$—Z$^1$)$_n$—[dioxane with X$^2$]—[cyclohexyl with X$^1$ and R$^2$]

| R$^1$ | (A$^1$—Z$^1$)$_n$ | X$^1$ | X$^2$ | R$^2$ |
|---|---|---|---|---|
| n-Propyl | [cyclohexyl] | —C≡C—C≡C—C(CH$_3$)$_3$ | H | CHFCF$_3$ |
| n-Pentyloxy | [cyclohexyl] | —C≡C—C≡C—C(CH$_3$)$_3$ | —C≡C—C≡C—C(CH$_3$)$_3$ | n-Propyl |

-continued

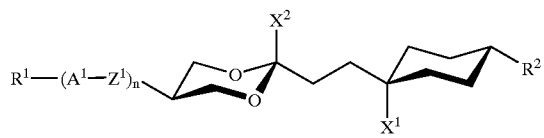

| R¹ | (A¹—Z¹)ₙ | X¹ | X² | R² |
|---|---|---|---|---|
| n-Propyl | 1,3-dioxane | —C≡C—C≡C—C(CH₃)₃ | H | OCF₃ |
| Ethoxy | cyclohexyl-CH₂CH₂-cyclohexyl | —C≡C—C≡C—Cl | H | F |
| n-Propyl | cyclohexyl-CF₂O— | —C≡C—C≡C—H | H | n-Propyl |
| n-Propyl | cyclohexyl-CF₂O— | —C≡C—C≡C—H | H | F |
| n-Propyl | cyclohexyl-CF₂O— | —C≡C—C≡C—H | H | CF₃ |
| n-Pentyl | cyclohexyl-CF₂O— | —C≡C—C≡C—H | H | n-Propyl |
| n-Pentyl | cyclohexyl-CF₂O— | —C≡C—C≡C—H | H | F |
| n-Pentyl | cyclohexyl-CF₂O— | —C≡C—C≡C—H | H | CF₃ |
| n-Hexyloxy | 1,3-dioxane-cyclohexyl | —C≡C—C≡C—C(CH₃)₃ | —C≡C—C≡C—CN | n-Propoxy |
| n-Pentyl | cyclohexyl | —C≡C—C≡C—CH₃ | H | n-Propyl |
| n-Propoxy | cyclohexyl | —C≡C—C≡C—Cl | H | CHFCF₃ |

The following compounds according to the invention are prepared analogously using the corresponding precursors:

| $R^1$ | $(A^1-Z^1)_n$ | $X^2$ | $R^2$ |
|---|---|---|---|
| n-Propyl | cyclohexyl | $-C\equiv C-C\equiv C-C(CH_3)_3$ | $CHFCF_3$ |
| n-Pentyloxy | cyclohexyl | $-C\equiv C-C\equiv C-C(CH_3)_3$ | n-Propyl |
| n-Propyl | 1,3-dioxane | $-C\equiv C-C\equiv C-Cl$ | $OCF_3$ |
| n-Hexyloxy | 1,3-dioxane-cyclohexyl | $-C\equiv C-C\equiv C-CF_3$ | n-Propoxy |
| n-Propyl | cyclohexyl | $-C\equiv C-C\equiv C-C(CH_3)_3$ | n-Propyl |
| n-Pentoxy | cyclohexyl | $-C\equiv C-C\equiv C-C(CH_3)_3$ | $CHFCF_3$ |
| n-Propyl | 1,3-dioxane | $-C\equiv C-C\equiv C-CH_3$ | $OCF_3$ |
| n-Propyl | cyclohexyl-$CF_2O$- | $-C\equiv C-C\equiv C-CH_3$ | n-Propyl |
| n-Propyl | cyclohexyl-$CF_2O$- | $-C\equiv C-C\equiv C-CH_3$ | F |
| n-Propyl | cyclohexyl-$CF_2O$- | $-C\equiv C-C\equiv C-CH_3$ | $CF_3$ |
| Vinyl | cyclohexyl | $-C\equiv C-C\equiv C-CH_3$ | n-Propyl |
| Vinyl | cyclohexyl | $-C\equiv C-C\equiv C-CH(C_2H_5)_2$ | n-Propyl |

The following compounds according to the invention are prepared analogously using the corresponding precursors:

| $R^1$ | $(Z^2-A^2)_m$ | $X^4$ | $R^2$ |
|---|---|---|---|
| n-Pentyloxy | cyclohexyl | —C≡C—C≡C—C(CH$_3$)$_3$ | n-Propyl |
| n-Propyl | 1,3-dioxane | —C≡C—C≡C—CH$_3$ | OCF$_3$ |
| n-Pentyl | bicyclohexyl | —C≡C—C≡C—C(CH$_3$)$_3$ | CF$_3$ |
| Ethyl | cyclohexyl-CH$_2$CH$_2$-cyclohexyl | —C≡C—C≡C—CF$_3$ | F |
| n-Hexyl | 1,3-dioxane-cyclohexyl | —C≡C—C≡C—C(CH$_3$)$_3$ | n-Propoxy |
| n-Pentyl | tricyclohexyl | —C≡C—C≡C—CH$_3$ | CF$_3$CF$_3$ |
| n-Pentyl | cyclohexyl | —C≡C—C≡C—CH$_3$ | n-Pentyloxy |
| n-Propoxy | cyclohexyl | —C≡C—C≡C—CF$_3$ | CHFCF$_3$ |

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A dialkyne compound of the formula I

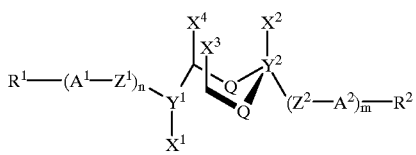

I in which $R^1$ and $R^2$, independently of one another, are H, F, or an alkyl radical having 1–15 carbon atoms which is unsubstituted or monosubstituted to perhalo substituted by halogen or substituted by CN and in which, one or more CH$_2$ groups are optionally, independently of one another, replaced by —O—, —S—, —CO—,

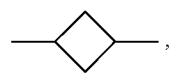

in such a way that heteroatoms are not connected directly, $X^1$, $X^2$, $X^3$ and $X^4$ are each, independently of one another, H or —C≡C—C≡C—R$^3$, provided that at least one of the groups $X^1$, $X^2$, $X^3$ and $X^4$ is —C≡C—C≡C—R$^3$, $R^3$ is H, Cl, CN, SF$_5$, CF$_3$, or an alkyl radical having 1–15 carbon atoms which is unsubstituted or monosubstituted to perhalo substituted by halogen and in which, one or more CR$_2$ groups are optionally replaced, in each case independently of one another, by —CH=CH— or —O— in such a way that —O— atoms are not connected directly, Q is —CH$_2$— or —O—, Y$^1$ and Y$^2$, independently of one another, are C or Si, A$^1$ and A$^2$, independently of one another, are a trans-1,4-cyclohexylene radical which is unsubstituted or substituted by F or CN and in which, one or more non-adjacent CH$_2$ groups are optionally replaced by —O— and/or —S—, or are

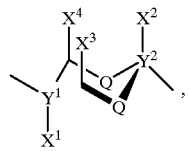

Z$^1$ and

Z$^2$ are each, independently of one another, —CO—O—, —O—CO—, 'CH$_2$O—, —O—, —OCH$_2$—, —CF$_2$O—, —OCF$_2$—, —CF$_2$CF$_2$—, —CF=CF—, —CH$_2$CH$_2$—, —CH=CH— or a single bond, and n and m, independently of one another, are 0, 1, 2 or 3, where m+n is 1, 2 or 3, excluding compounds wherein X$^2$ is —C≡C—C≡C—R$^3$; R$^3$ is H; X$^1$, X$^3$ and X$^4$ are H; each Q is CH$_2$; m is 0; Y$^1$ and Y$^2$ are each C; n is 1, Z$^1$ is a single bond and A$^1$ is unsubsrituted trans-1,4-cyclohexylene; and excluding compounds wherein X$^1$ is —C≡C—C≡C—R$^3$; R$^3$ is H; X$^2$, X$^3$ and X$^4$ are H; each O is CH$_2$; n is 0; Y$^1$ and Y$^2$ are each C; m is 1, Z$^2$ is a single bond and A$^2$ is unsubstituted trans-1,4-cyclohexylene.

2. A dialkyne compound according to claim 1, which exhibits an optical anisotropy value M of <0.03 at a reduced temperature of 0.9 and a wavelength of 589 nm.

3. A dialkyne compound according to claim 1, wherein Y$^1$ and Y$^2$ are C.

4. A dialkyne compound according to claim 1, wherein m and n are 0, 1 or 2.

5. A dialkyne compound according to claim 1, wherein Z$^1$ and Z$^2$, independently of one another, are —CN$_2$CH$_2$—, —COO—, —OOC—, —CF$_2$O—, —OCF$_2$— or a single bond.

6. A dialkyne compound according to claim 1, wherein R$^1$ and R$^2$ are simultaneously straight-chain alkyl or alkoxy having 1 to 10 carbon atoms.

7. A dialkyne compound according to claim 1, wherein X$^1$, X$^2$, X$^3$ and/or X$^4$ are —C≡C—C≡C—CH(alkyl*)$_2$, —C≡C—C≡C—C(alkyl*)(alkyl**)$_2$ or —C≡C—C≡C—C(alkyl*)$_3$, where alkyl* and alkyl** are each, independently of one another, CH$_3$, C$_2$H$_5$ or C$_3$H$_7$.

8. A dialkyne compound according to claim 1, wherein X$^3$ and X$^4$ are simultaneously H.

9. A liquid-crystalline medium having at least two liquid-crystalline components, which comprises at least one compound of the formula I of claim 1.

10. A liquid-crystal display element, which comprises a liquid-crystalline medium according to claim 9.

11. A reflective or transfective liquid-crystal display element, which comprises as dielectric, a liquid-crystalline medium according to claim 9.

12. An electro-optical display element, which comprises, as dielectric, a liquid-crystalline medium according to claim 9.

13. A dialkyne compound according to claim 1, wherein one of X$^1$, X$^2$, X$^3$ or X$^4$ is —C≡C—C≡C—H, —C≡C—C≡C-alkyl, —C≡C—C≡C—Cl or —C≡C—C≡C—CN, where alkyl is an alkyl radical having to 1 to 15 carbon atoms.

14. A dialkyne compound according to claim 1, wherein one of X$^1$, X$^2$, X$^3$ or X$^4$ is —C≡C—C≡C-alkyl where the alkyl radical is branched.

15. A dialkyne compound according to claim 1, wherein one of X$^1$, X$^2$, X$^3$ or X$^4$ is —C≡C—C≡C-alkyl where the alkyl radical is tert-butyl.

16. A dialkyne compound according to claim 1, wherein the compound is of one of the following formulae I1 to I21:

I1
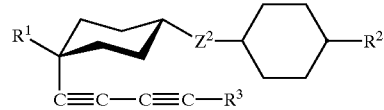

I2
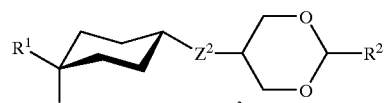

I3
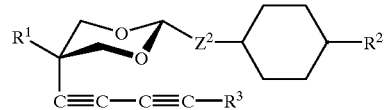

I4
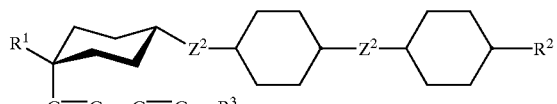

I5

I6
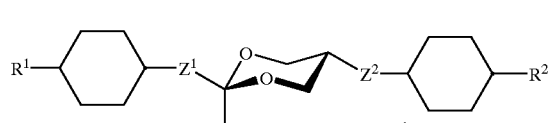

I7
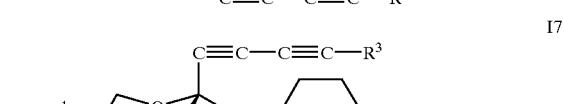

I8
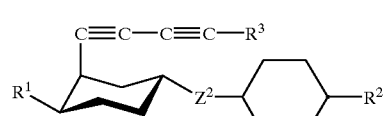

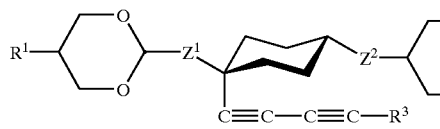
I9
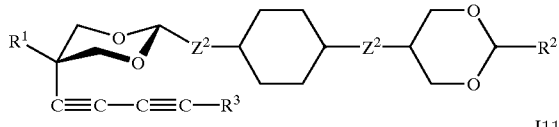
I10
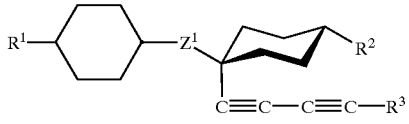
I11
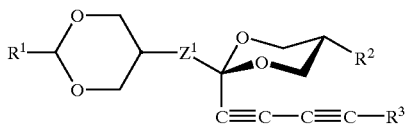
I12
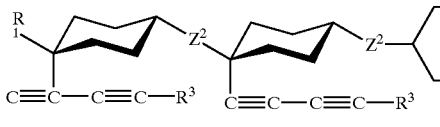
I13
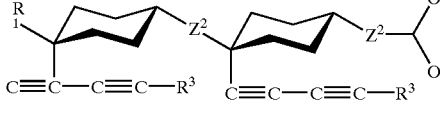
I14
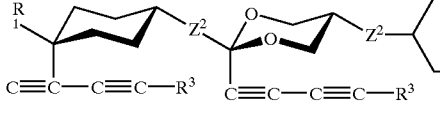
I15
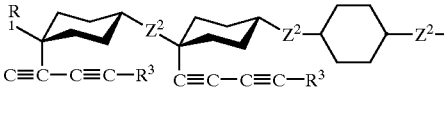
I16
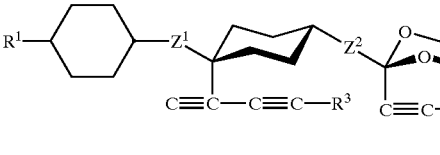
I17
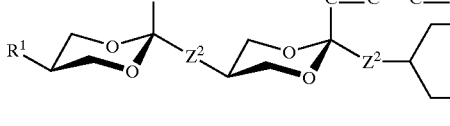
I18
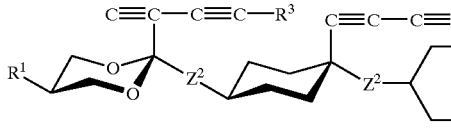
I19
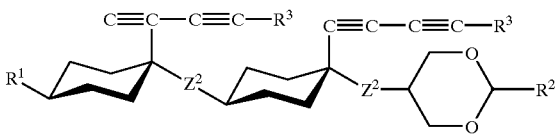
I20
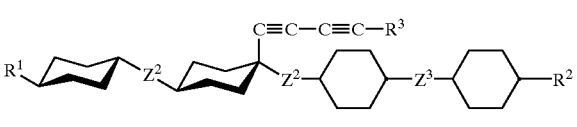
I21
in which $R^1$, $R^2$, $R^3$, $Z^1$, and $Z^2$ are as defined above and $Z^3$ is independently as defined for $Z^1$ and $Z^2$.
17. A dialkyne compound according to claim 1, wherein the compound is of one of formulae I22 to I36:
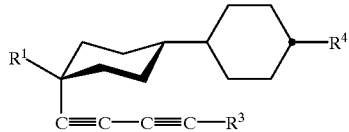
I22
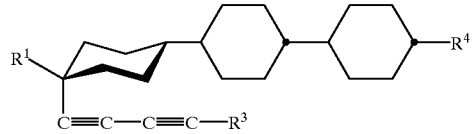
I23
I24
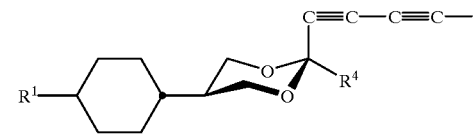
I25
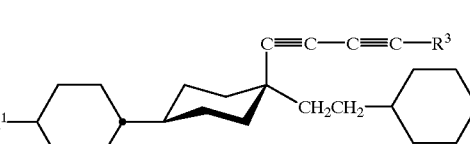
I26
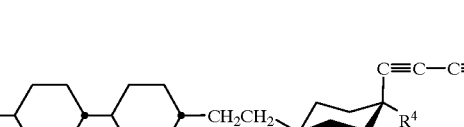
I27
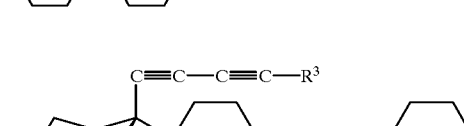
I28

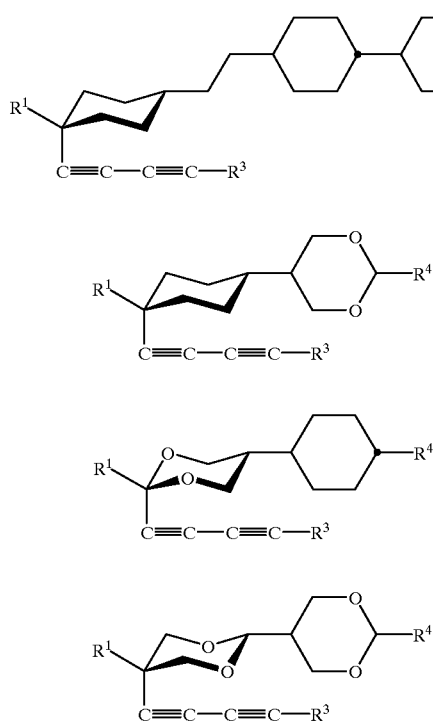
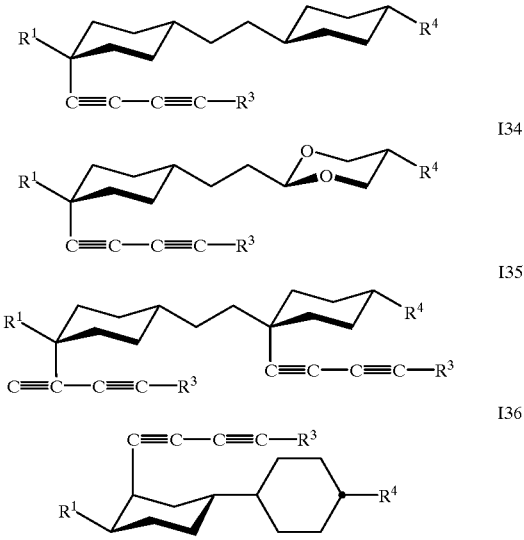
in which $R^1$ and $R^3$ are as defined above, and $R^4$ is alkyl, alkenyl or alkoxy.
18. A liquid-crystalline medium according to claim 9, wherein the medium comprises from 1 to 40% of compounds of the formula I.
19. A liquid-crystalline medium according to claim 9, wherein the medium comprises more than 40% of compounds of the formula I.
* * * * *

UNITED STATES PATENT AND TRADEMARK OFFICE
CERTIFICATE OF CORRECTION

PATENT NO.    : 6,632,484 B2
DATED         : October 14, 2003
INVENTOR(S)   : Volker Reiffenrath et. al.

It is certified that error appears in the above-identified patent and that said Letters Patent is hereby corrected as shown below:

Column 42,
Line 58, reads "in such a way" should read -- CO-O-, -O-CO-, -O-CO-O- or -CH=CH- in
such a way --

Column 43,
Line 1, reads "$CR_2$ groups" should read -- $CH_2$ groups --
Line 23, reads " '$CH_2O$-," should read -- -$CH_2O$-, --
Line 33, reads "unsubsrituted" should read -- unsubstituted --
Line 36, reads "each O is" should read -- each Q is --
Line 40, reads "M" should read -- $\Delta n$ --
Line 47, reads "are -$CN_2CH_2$-," should read -- are --$CH_2CH_2$-, --

Signed and Sealed this

Thirty-first Day of August, 2004

JON W. DUDAS
*Director of the United States Patent and Trademark Office*